US006632977B2

(12) United States Patent
Kieffer et al.

(10) Patent No.: US 6,632,977 B2
(45) Date of Patent: Oct. 14, 2003

(54) TRANSGENIC ANIMAL WHOSE EXPRESSION OF THE OPIATE RECEPTORS IS MODIFIED

(75) Inventors: Brigitte Kieffer, Erstein (FR); Hans W. D. Matthes, Illkirch (FR); Frederic Herve Simonin, Bischheim (FR); Andree Dierich, Strasbourg (FR); Marianne Lemeur, Strasbourg (FR)

(73) Assignee: Centre National de la Recherche Scientifique, Paris (FR)

( * ) Notice: Subject to any disclaimer, the term of this patent is extended or adjusted under 35 U.S.C. 154(b) by 84 days.

(21) Appl. No.: 09/214,904

(22) PCT Filed: Jul. 11, 1997

(86) PCT No.: PCT/FR97/01282

§ 371 (c)(1),
(2), (4) Date: Mar. 11, 1999

(87) PCT Pub. No.: WO98/02534

PCT Pub. Date: Jan. 22, 1998

(65) Prior Publication Data

US 2001/0047519 A1 Nov. 29, 2001

(30) Foreign Application Priority Data

Jul. 15, 1996 (FR) .............................. 96 08810

(51) Int. Cl.[7] .................... A01K 67/00; A01K 67/0633; A01K 67/027; G01N 33/00
(52) U.S. Cl. ................................ 800/18; 800/3; 800/9; 800/13
(58) Field of Search ................... 800/14, 8, 3; 536/23.1, 536/24.1, 24.31; 514/44; 435/320.1, 325, 455

(56) References Cited

U.S. PATENT DOCUMENTS 5,487,992 A * 6/1993 Capecchi et al. ......... 435/172.3

FOREIGN PATENT DOCUMENTS

| WO | WO 93/21309 | 10/1993 |
| WO | WO 95/07983 | 3/1995 |
| WO | WO 96/01898 | 1/1996 |

OTHER PUBLICATIONS

R Elde et al., Distribution of Neuropeptide Receptors,"New Views of Peptidergic Neurotransmission Made Possible by Antibodies to Opioid Receptors," pp. 390–404.*
Sora et al. Proceedings of the National Academy of Science, USA 94:1544–1549, Feb. 1997.*
Matthes et al. Nature 383:819–823, Oct. 1996.*
Lee et al. WO 93/21309 (PCT/US93/02913), Oct. 1993.*
Hammer et al. Journal of Animal Science 63(1):269–78, Jul. 1986.*
Ebert et al. Molecular Endocrinology 2(3):277–283, Mar. 1988.*
Elde et al. Annals of New York Academy of Science 757:390–404, May 1995.*
Ryan et al. The Journal of Cell Biology 134(5):1219–1227, Sep. 1996.*
Ip et al. The Journal of Neuroscience 13(8):3394–3405, Aug. 1993.*
by H.W.D. Matthes et al., "Loss of morphine–induced anal–gesia, reward effect and withdrawal symptoms in mice lacking the μ–opioid–receptor gene", Nature, vol. 383, No. 6603, Oct. 31, 1996, London, pp. 819–823.

* cited by examiner

Primary Examiner—Deborah Crouch
Assistant Examiner—Joseph Woitach
(74) Attorney, Agent, or Firm—Young & Thompson

(57) ABSTRACT

The invention concerns the use of a non-human transgenic mammal whose expression of a gene coding for an opiate receptor is modified, particularly in the nerve tissues with respect to a normal expression, in particular in the nerve tissues, for producing a medicine for the treatment of pathological conditions involving opiate receptors, in particular severe acute or chronic pains, drug addiction or the prevention or the treatment of transplant rejections.

13 Claims, 20 Drawing Sheets

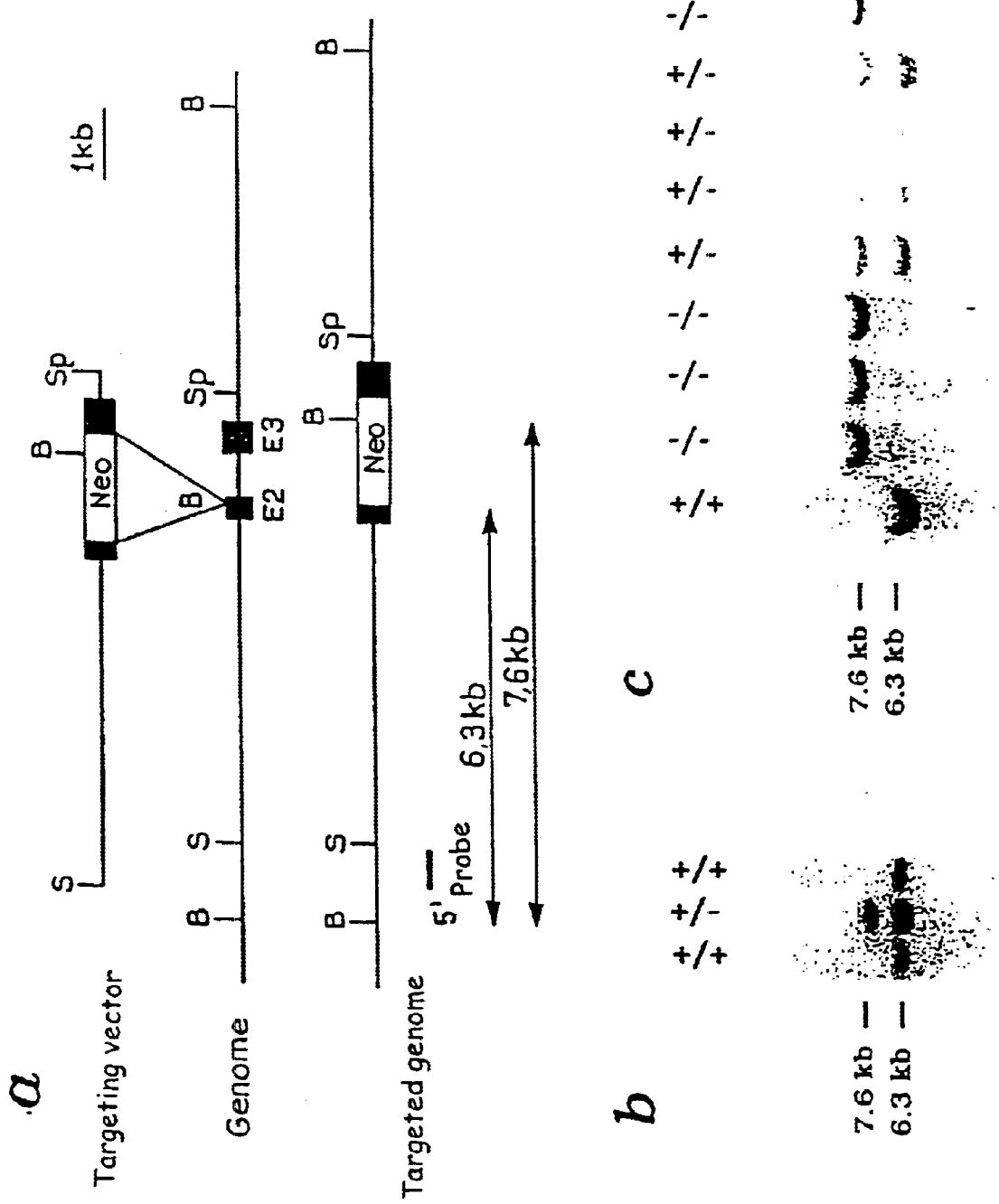

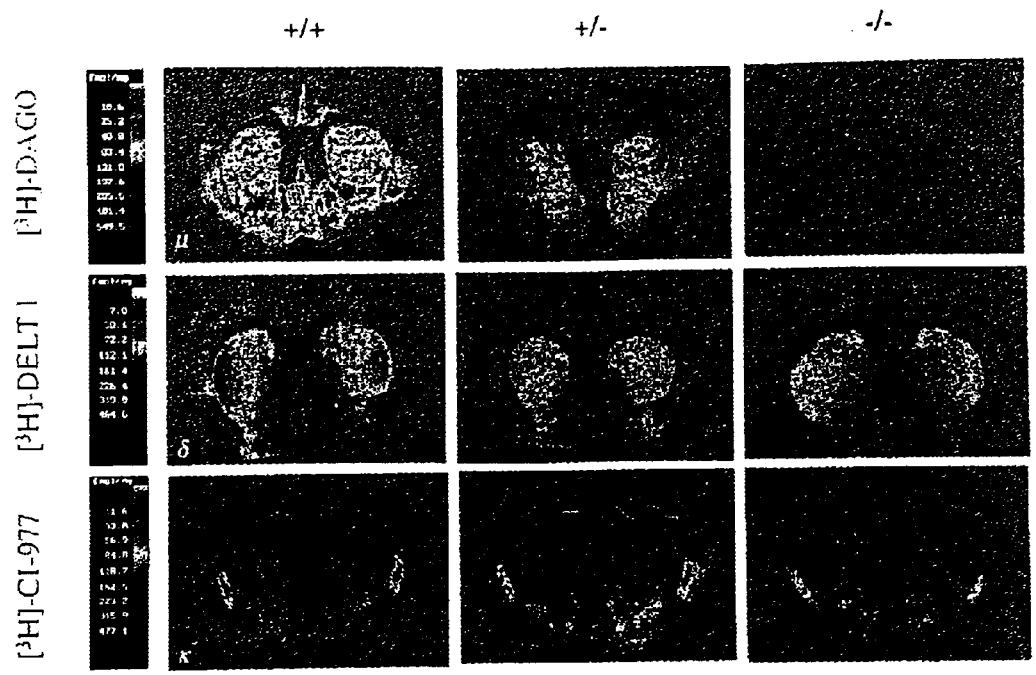
Figure 2 B
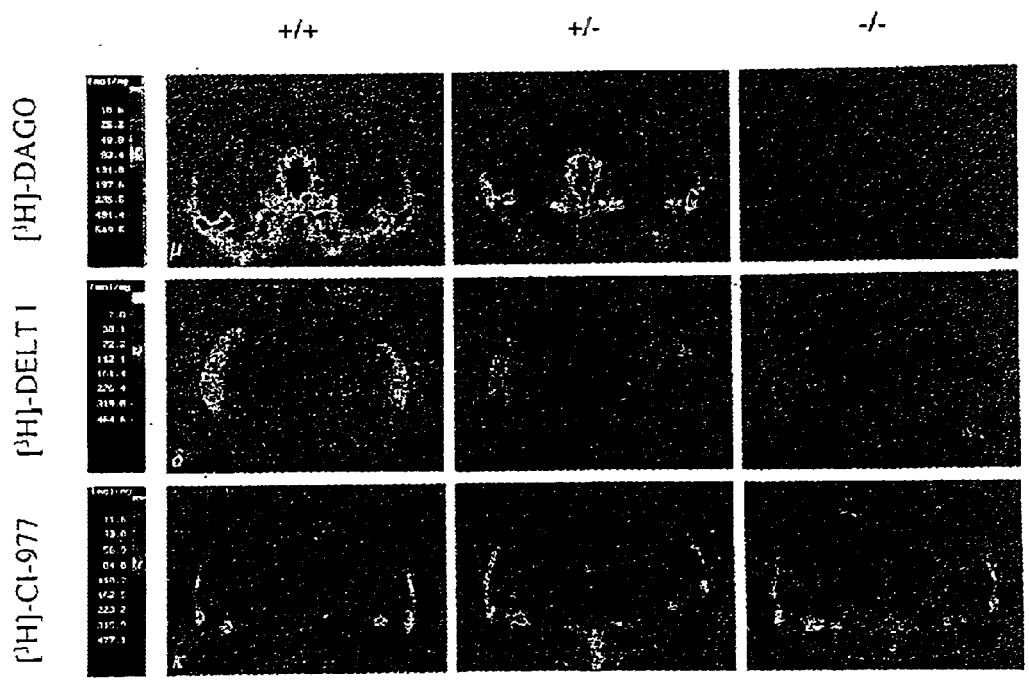
Figur 2 C

FIG. 3A
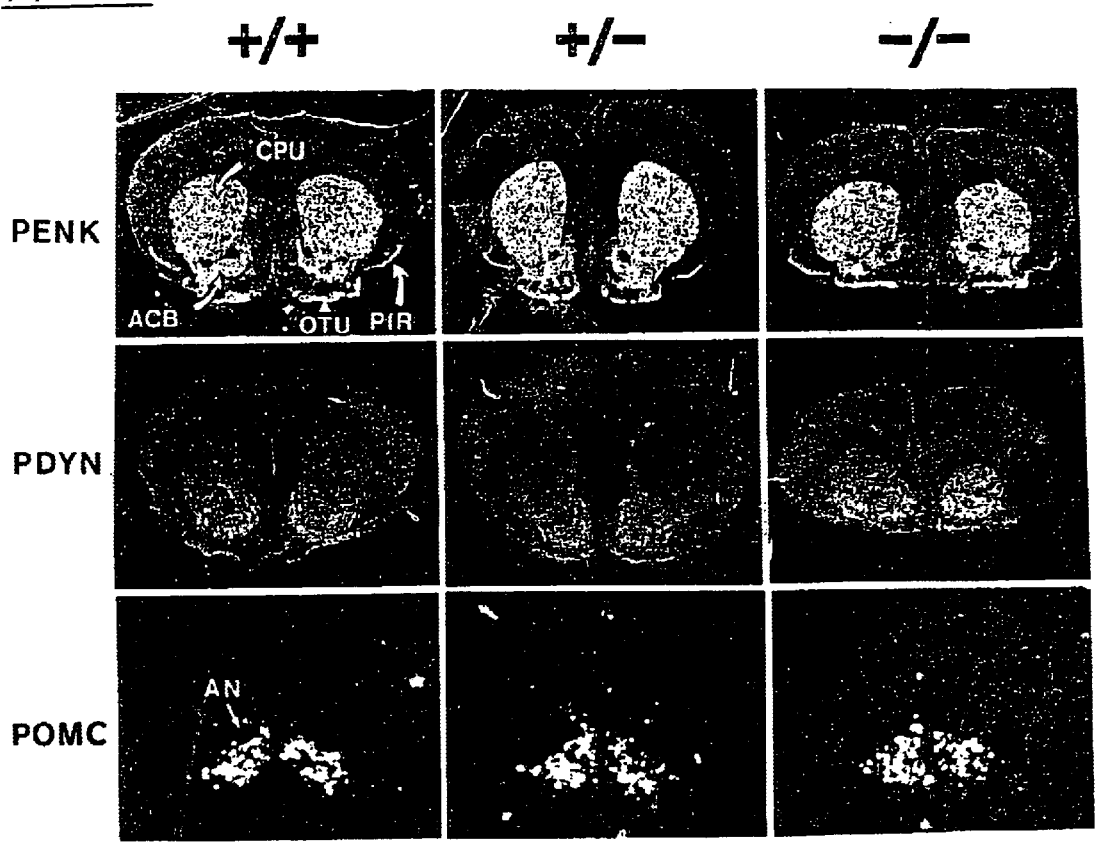
FIG. 3B

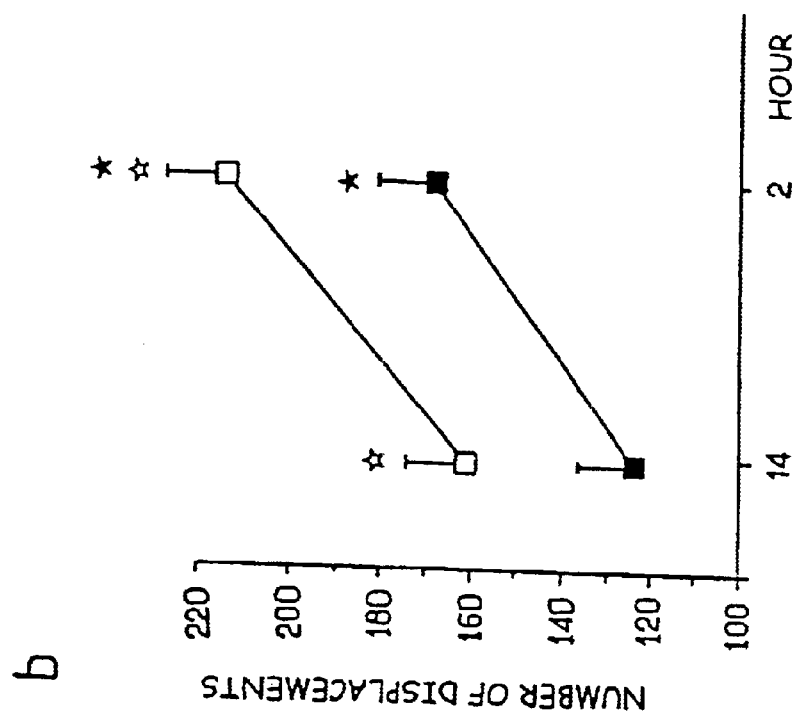
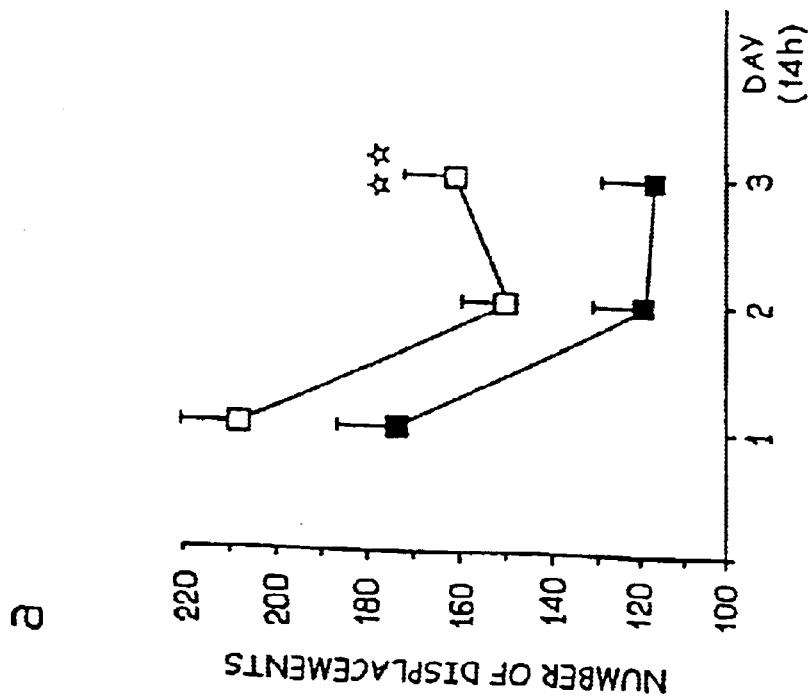
FIG_4

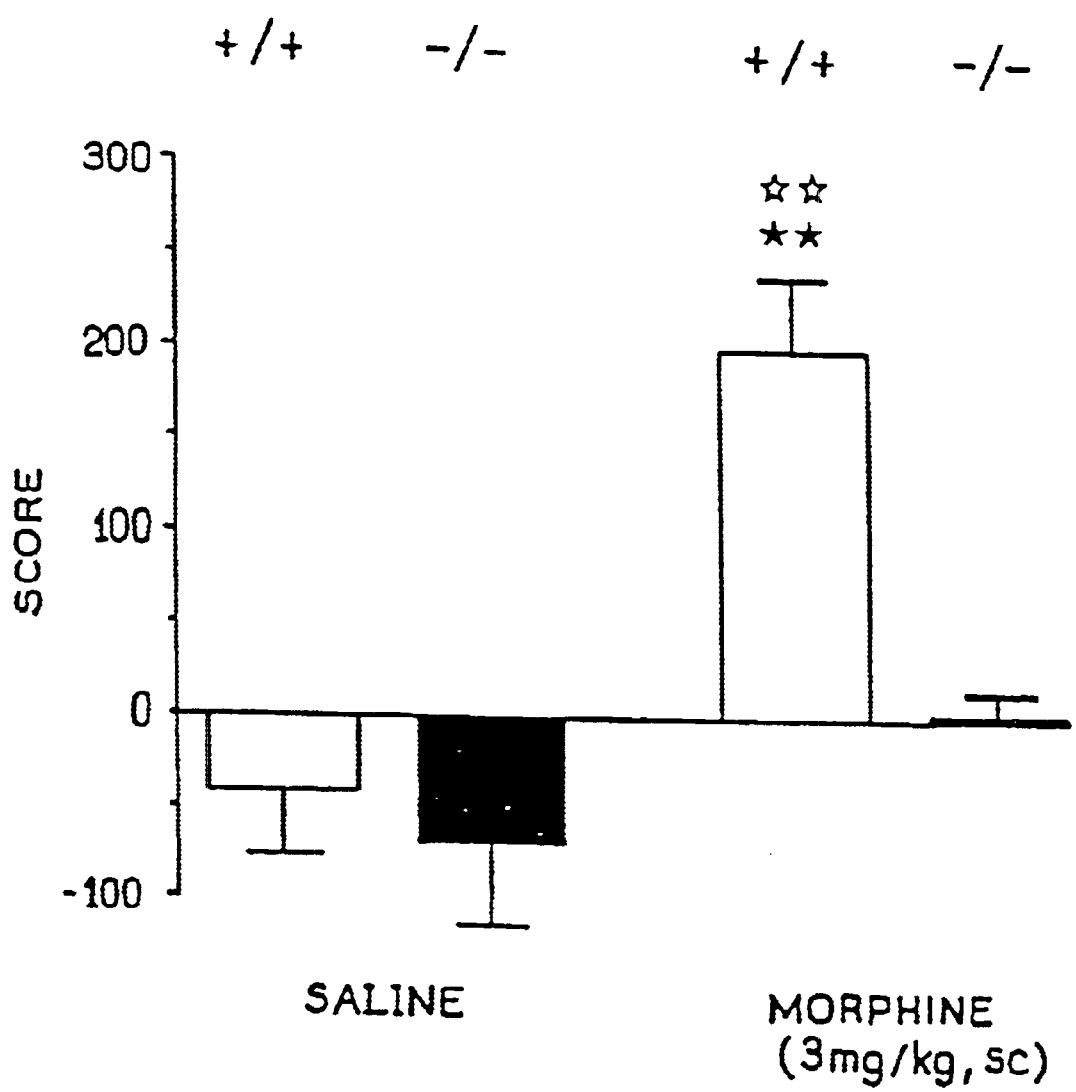
FIG_6 b  FIG. 7B
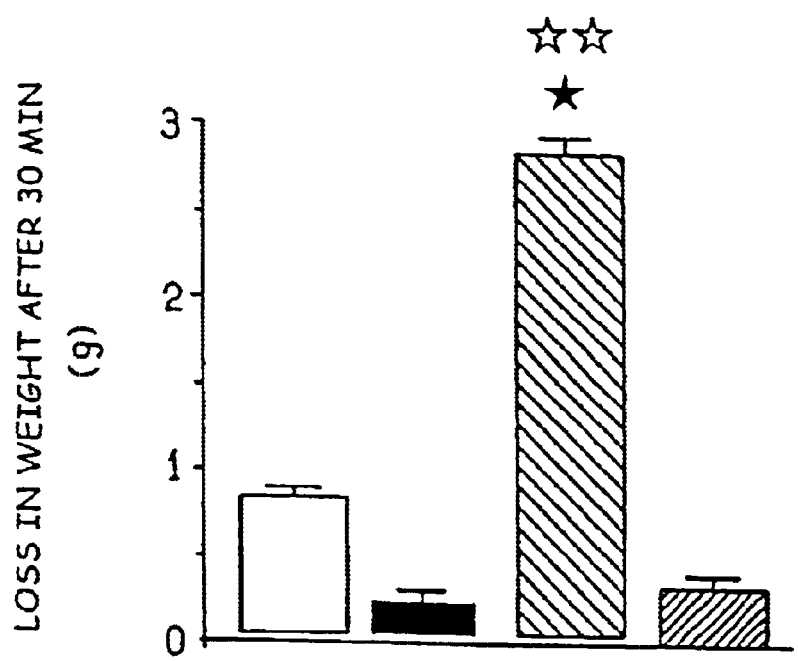
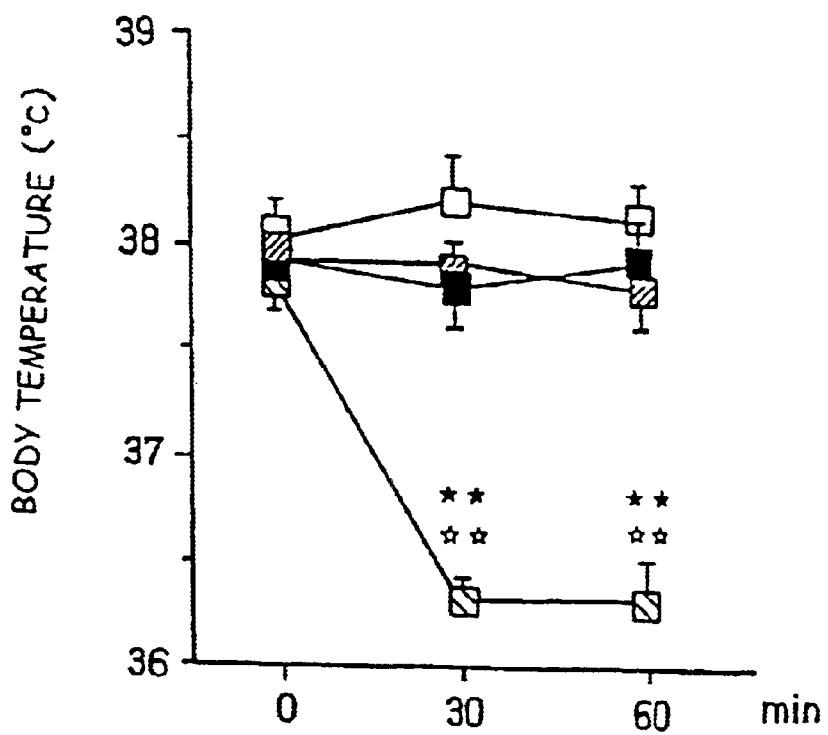

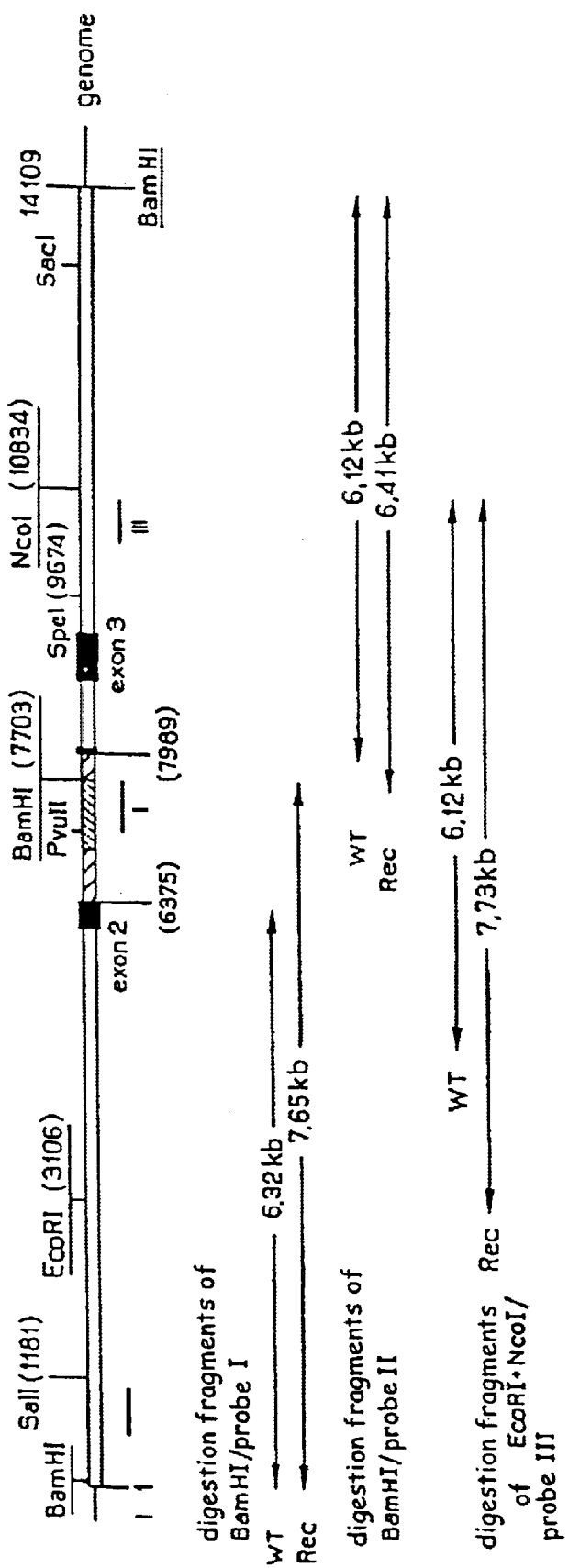
FIG_8

FIG_9
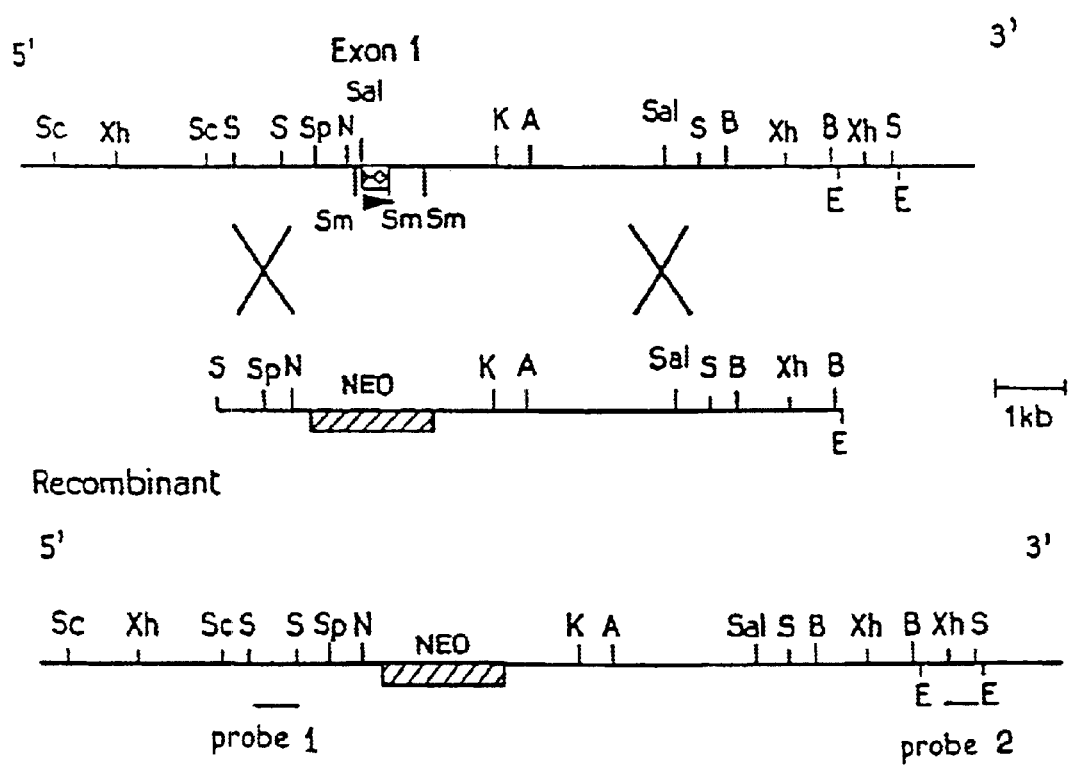

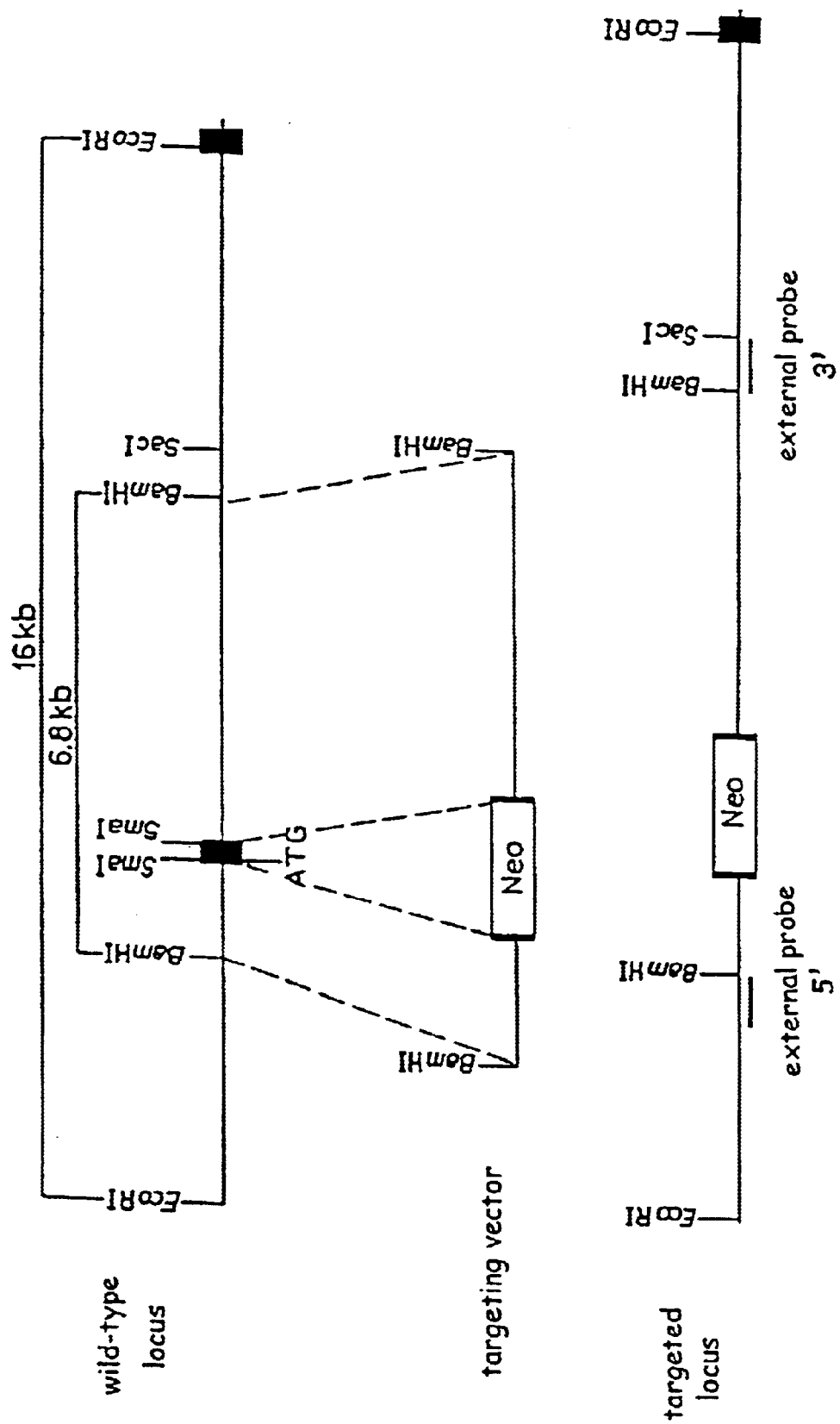

mMOR

```
1/1                                           31/11
CGG ATC CTT AGC ATC CCC AAA GCG CCT CCG TGT ACT TCT AAG GTG GGA GGG GGA TAC AAG
61/21                                         91/31
CAG AGG AGA ATA TCG GAC GCT CAG ACG TTC CAT TCT GCC TGC CGC TCT TCT CTG GTT CCA
121/41                                        151/51
CTA GGG CTT GTC CTT GTA AGA AAC TGA CGG AGC CTA GGG CAG CTG TGA GAG GAA GAG GCT
181/61                                        211/71
GGG GCG CCT GGA ACC CGA ACA CTC TTG AGT GCT CTC AGT TAC AGC CTA CCG AGT CCG CAG
241/81                                        271/91
CAA GCA TTC AGA ACC ATG GAC AGC AGC GCC GGC CCA GGG AAC ATC AGC GAC TGC TCT GAC
                    met asp ser ser ala gly pro gly asn ile ser asp cys ser asp
301/101                                       331/111
CCC TTA GCT CCT GCA AGT TGG TCC CCA GCA CCT GGC TCC TGG CTC AAC TTG TCC CAC GTT
pro leu ala pro ala ser trp ser pro ala pro gly ser trp leu asn leu ser his val
361/121                                       391/131
GAT GGC AAC CAG TCC GAC CCA TGC GGT CCT AAC CGC ACG GGG CTT GGC GGG AGC CAC AGC
asp gly asn gln ser asp pro cys gly pro asn arg thr gly leu gly gly ser his ser
421/141                                       451/151
CTG TGC CCT CAG ACC GGC AGC CCT TCC ATG GTC ACA GCC ATC ACC ATC ATG GCC CTC TAT
leu cys pro gln thr gly ser pro ser met val thr ala ile thr ile met ala leu tyr
481/161                                       511/171
TCT ATC GTG TGT GTA GTG GGC CTC TTT GGA AAC TTC CTG GTC ATG TAT GTG ATT GTA AGA
ser ile val cys val val gly leu phe gly asn phe leu val met tyr val ile val arg
541/181                                       571/191
TAT ACC AAA ATG AAG ACT GCC ACC AAC ATC TAC ATT TTC AAC CTT GCT CTG GCA GAT GCC
tyr thr lys met lys thr ala thr asn ile tyr ile phe asn leu ala leu ala asp ala
601/201                                       631/211
TTA GCC ACT AGC ACG CTG CCC TTT CAG AGT GTT AAC TAC CTG ATG GGA ACG TGG CCC TTT
leu ala thr ser thr leu pro phe gln ser val asn tyr leu met gly thr trp pro phe
661/221                                       691/231
GGA AAC ATC CTC TGC AAG ATC GTG ATC TCA ATA GAC TAC TAC AAC ATG TTC ACC AGT ATC
gly asn ile leu cys lys ile val ile ser ile asp tyr tyr asn met phe thr ser ile
721/241                                       751/251
TTC ACC CTC TGC ACC ATG AGT GTA GAC CGC TAC ATT GCC GTC TGC CAC CCG GTC AAG GCC
phe thr leu cys thr met ser val asp arg tyr ile ala val cys his pro val lys ala
781/261                                       811/271
CTG GAT TTC CGT ACC CCC CGA AAT GCC AAA ATT GTC AAT GTC TGC AAC TGG ATC CTC TCT
leu asp phe arg thr pro arg asn ala lys ile val asn val cys asn trp ile leu ser
841/281                                       871/291
TCT GCC ATT GGT CTG CCC GTA ATG TTC ATG GCA ACC ACA AAA TAC AGG CAG GGG TCC ATA
ser ala ile gly leu pro val met phe met ala thr thr lys tyr arg gln gly ser ile
901/301                                       931/311
GAT TGC ACC CTC ACT TTC TCT CAT CCC ACA TGG TAC TGG GAG AAC CTG CTC AAA ATC TGT
asp cys thr leu thr phe ser his pro thr trp tyr trp glu asn leu leu lys ile cys
```

Figure 11

```
961/321                              991/331
GTC TTC ATC TTC GCC TTC ATC ATG CCG GTC CTC ATC ATC ACT GTG TGT TAT GGA CTG ATG
val phe ile phe ala phe ile met pro val leu ile ile thr val cys tyr gly leu met
1021/341                             1051/351
ATC TTA CGA CTC AAG AGT GTC CGC ATG CTG TCG GGC TCC AAA GAA AAG GAC AGG AAC CTG
ile leu arg leu lys ser val arg met leu ser gly ser lys glu lys asp arg asn leu
1081/361                             1111/371
CGC AGG ATC ACC CGG ATG GTG CTG GTG GTC GTG GCT GTA TTT ATT GTC TGC TGG ACC CCC
arg arg ile thr arg met val leu val val val ala val phe ile val cys trp thr pro
1141/381                             1171/391
ATC CAC ATC TAT GTC ATC ATC AAA GCA CTG ATC ACG ATT CCA GAA ACC ACT TTC CAG ACT
ile his ile tyr val ile ile lys ala leu ile thr ile pro glu thr thr phe gln thr
1201/401                             1231/411
GTT TCC TGG CAC TTC TGC ATT GCC TTG GGT TAC ACA AAC AGC TGC CTG AAC CCA GTT CTT
val ser trp his phe cys ile ala leu gly tyr thr asn ser cys leu asn pro val leu
1261/421                             1291/431
TAT GCG TTC CTG GAT GAA AAC TTC AAA CGA TGT TTT AGA GAG TTC TGC ATC CCA ACT TCC
tyr ala phe leu asp glu asn phe lys arg cys phe arg glu phe cys ile pro thr ser
1321/441                             1351/451
TCC ACA ATC GAA CAG CAA AAC TCT GCT CGA ATC CGT CAA AAC ACT AGG GAA CAC CCC TCC
ser thr ile glu gln gln asn ser ala arg ile arg gln asn thr arg glu his pro ser
1381/461                             1411/471
ACG GCT AAT ACA GTG GAT CGA ACT AAC CAC CAG CTA GAA AAT CTG GAA GCA GAA ACT GCT
thr ala asn thr val asp arg thr asn his gln leu glu asn leu glu ala glu thr ala
1441/481                             1471/491
CCA TTG CCC TAA CTG GGT CCC ACG CCA TCC AGA CCC TCG CTA AAC TTA GAG GCT GCC ATC
pro leu pro
1501/501                             1531/511
TAC TTG GAA TCA GGT TGC TGT CAG GGT TTG TGG GAG GCT CTG GTT TCC TGG AAA AGC ATC
1561/521                             1591/531
TGA TCC TGC ATC ATT CAA AGT CAT TCC TCT CTG GCT ATT CAC GCT ACA CGT CAG AGA CAC
1621/541                             1651/551
TCA GAC TGT GTC AAG CAC TCA GAA GGA AGA GAC TGC AGG CCA CTA CTG AAT CCA GCT CAT
1681/561                             1711/571
GTA CAG AAA CAT CCA ATG GAC CAC AAT ACT CTG TGG TAT GTG ATT TGT GAT CAA CAT AGA
1741/581                             1771/591
AGG TGA CCC TTC CCT ATG TGG AAT TTT TAA TTT CAA GGA AAT ACT TAT GAT CTC ATC AAG
1801/601                             1831/611
GGA AAA ATA GAT GTC ACT TGT TAA ATT CAC TGT AGT GAT GCA TAA AGG AAA AGC TAC CTC
1861/621                             1891/631
TGA CCT CTA GCC CAG TCA CCC TCT ATG GAA AGT TCC ATA GGG AAT ATG TGA GGG AAA ATG
1921/641                             1951/651
TTG CTT CCA AAT TAA ATT TTC ACC TTT ATG TTA TAG TCT AGT TAA GAC ATC AGG GGC ATC
1981/661                             2011/671
TCT GTT TCT TGG TTT TGT ATT GTT TGA AAG AAG ACA TCT TCC TCC CTA GCT GCG TGT TGA
2041/681                             2071/691
AAA TGA AAG GGA TTT AAA ACA CAG TGT CAA CTG CAG AAT AGT TGA TTC TCG CAC TGA AGG
```

Figure 11 (continuation 1)

```
2101/701                                      2131/711
GGG GGG GCT AAT CTT CCC AAT TCT TTC CAT GTC CTC CAA GTG TTC ACA AGG TCA AAC TCA
2161/721                                      2191/731
GAG TCA CCC AGT AAG CTC ATC ATG CCA CCA TTC TGA GCA AAA TCC TTG GAT TCC TGC TCA
2221/741
GAA TGG TGG
```

Figure 11 (continuation 2)

mDOR

```
1/1                                            31/11
TCT AAA GGC TGG GTC CCT GCG CCC AGG GCG CAC GGT GGA GAC GGA CAC GGC GGC GCC ATG
                                                                                met 61/21                                          91/31
GAG CTG GTG CCC TCT GCC CGT GCG GAG CTG CAG TCC TCG CCC CTC GTC AAC CTC TCG GAC
glu leu val pro ser ala arg ala glu leu gln ser ser pro leu val asn leu ser asp 121/41                                         151/51
GCC TTT CCC AGC GCC TTC CCC AGC GCG GGC GCC AAT GCG TCG GGG TCG CCG GGA GCC CGT
ala phe pro ser ala phe pro ser ala gly ala asn ala ser gly ser pro gly ala arg 181/61                                         211/71
AGT GCC TCG TCC CTC GCC CTA GCC ATC GCC ATC ACC GCG CTC TAC TCG GCT GTG TGC GCA
ser ala ser ser leu ala leu ala ile ala ile thr ala leu tyr ser ala val cys ala 241/81                                         271/91
GTG GGG CTT CTG GGC AAC GTG CTC GTC ATG TTT GGC ATC GTC CGG TAC ACC AAA TTG AAG
val gly leu leu gly asn val leu val met phe gly ile val arg tyr thr lys leu lys 301/101                                        331/111
ACC GCC ACC AAC ATC TAC ATC TTC AAT CTG GCT TTG GCT GAT GCG CTG GCC ACC AGC ACG
thr ala thr asn ile tyr ile phe asn leu ala leu ala asp ala leu ala thr ser thr 361/121                                        391/131
CTG CCC TTC CAG AGC GCC AAG TAC TTG ATG GAA ACG TGG CCG TTT GGC GAG CTG CTG TGC
leu pro phe gln ser ala lys tyr leu met glu thr trp pro phe gly glu leu leu cys 421/141                                        451/151
AAG GCT GTG CTC TCC ATT GAC TAC TAC AAC ATG TTC ACT AGC ATC TTC ACC CTC ACC ATG
lys ala val leu ser ile asp tyr tyr asn met phe thr ser ile phe thr leu thr met 481/161                                        511/171
ATG AGC GTG GAC CGC TAC ATT GCT GTC TGC CAT CCT GTC AAA GCC CTG GAC TTC CGG ACA
met ser val asp arg tyr ile ala val cys his pro val lys ala leu asp phe arg thr 541/181                                        571/191
CCA GCC AAG GCC AAG CTG ATC AAT ATA TGC ATC TGG GTC TTG GCT TCA GGT GTC GGG GTC
pro ala lys ala lys leu ile asn ile cys ile trp val leu ala ser gly val gly val 601/201                                        631/211
CCC ATC ATG GTC ATG GCA GTG ACC CAA CCC CGG GAT GGT GCA GTG GTA TGC ATG CTC CAG
pro ile met val met ala val thr gln pro arg asp gly ala val val cys met leu gln 661/221                                        691/231
TTC CCC AGT CCC AGC TGG TAC TGG GAC ACT GTG ACC AAG ATC TGC GTG TTC CTC TTT GCC
phe pro ser pro ser trp tyr trp asp thr val thr lys ile cys val phe leu phe ala 721/241                                        751/251
TTC GTG GTG CCG ATC CTC ATC ATC ACG GTG TGC TAT GGC CTC ATG CTA CTG CGC CTG CGC
phe val val pro ile leu ile ile thr val cys tyr gly leu met leu leu arg leu arg
```

Figure 12

```
781/261                                    811/271
AGC GTG CGT CTG CTG TCC GGT TCC AAG GAG AAG GAC CGC AGC CTG CGG CGC ATC ACG CGC
ser val arg leu leu ser gly ser lys glu lys asp arg ser leu arg arg ile thr arg 841/281                                    871/291
ATG GTG CTG GTG GTG GTG GGC GCC TTC GTG GTG TGC TGG GCG CCC ATC CAC ATC TTC GTC
met val leu val val val gly ala phe val val cys trp ala pro ile his ile phe val 901/301                                    931/311
ATC GTC TGG ACG CTG GTG GAC ATC AAT CGG CGC GAC CCA CTT GTG GTG GCC GCA CTG CAC
ile val trp thr leu val asp ile asn arg arg asp pro leu val val ala ala leu his 961/321                                    991/331
CTG TGC ATT GCG CTG GGC TAC GCC AAC AGC AGC CTC AAC CCG GTT CTC TAC GCC TTC CTG
leu cys ile ala leu gly tyr ala asn ser ser leu asn pro val leu tyr ala phe leu 1021/341                                   1051/351
GAC GAG AAC TTC AAG CGC TGC TTC CGC CAG CTC TGT CGC ACG CCC TGC GGC CGC CAA GAA
asp glu asn phe lys arg cys phe arg gln leu cys arg thr pro cys gly arg gln glu 1081/361                                   1111/371
CCC GGC AGT CTC CGT CGT CCC CGC CAG GCC ACC ACG CGT GAG CGT GTC ACT GCC TGC ACC
pro gly ser leu arg arg pro arg gln ala thr thr arg glu arg val thr ala cys thr 1141/381                                   1171/391
CCC TCC GAC GGC CCG GGC GGT GGC GCT GCC GCC TGA CCT ACC CGA CCT TCC CCT TAA ACG
pro ser asp gly pro gly gly gly ala ala ala *

1201/401                                   1231/411
CCC CTC CCA AGT GAA GTG ATC CAG AGG CCA CAC CGA GCT CCC TGG GAG GCT GTG GCC ACC

1261/421                                   1291/431
ACC AGG ACA GCT AGA ATT GGG CCT GCA CAG AGG GGA GGC CTC CTG TGG GGA CGG GGC CTG

1321/441                                   1351/451
AGG GAT CAA AGG CTC CAG GTT GGA ACG GTG GGG GTG AGG AAG CAG AGC TGG TGA TTC CTA

1381/461                                   1411/471
AAC TGT ATC CAT TAG TAA GGC CTC TCC AAT GGG ACA GAG CCT CCG CCT TGA GAT AAC ATC

1441/481                                   1471/491
GGG TTC TGG CCT TTT TGA ACA CCC AGC TCC AGT CCA AGA CCC AAG GAT TCC AGC TCC AGG

1501/501                                   1531/511
AAC CAG GAG GGG CAG TGA TGG GGT CGA TGA TTT GGT TTG GCT GAG AGT CCC AGC ATT TGT

1561/521                                   1591/531
GTT ATG GGG AGG ATC TCT CAT CTT AGA GAA GAT AAG GGG ACA GGG CAT TCA GGC AAG GCA
```

Figure 12 (continuation 1)

```
1621/541                                    1651/551
GCT TGG GGT TTG GTC AGG AGA TAA GCG CCC CCT TCC CTT GGG GGG AGG ATA AGT GGG GGA
1681/561                                    1711/571
TGG TCA ACG TTG GAG AAG AGT CAA AGT TCT CAC CAC CTT TCT AAC TAC TCA GCT AAA CTC
1741/581                                    1771/591
GTT GAG GCT AGG GCC AAC GTG ACT TCT CTG TAG AGA GGA TAC AAG CCG GCT CTG ATG GGG
1801/601                                    1831/611
CAG GCC TGT GTA ATC CCA GTC ATA GTG GAG GCT GAG GCT GGA AAA TTA AGG ACC AAC AGC
1861/621                                    1891/631
CTG GGC AAT TTA GTG TCT CAA AAT AAA ATG TAA AGA GGG CTG GGA ATG TAG CTC AGT GGT
1921/641                                    1951/651
AGG GTG TTT GTG TGA GGC TCT GGG ATC AAT AAG ACA AAA CAA CCA ACC AAC CAA AAA CCT
1981/661                                    2011/671
TCC AAA CAA CAA AAC CAA CCC TCA AAC CAA AAA ACT ATG TGG GTG TCT CTG AGT CTG GTT
2041/681                                    2071/691
TGA AGA GAA CCC GCA GCC CTG TAT CCC TGT GGG GCT GTG GAC AGT GGG CAG AAG CAG AGG
2101/701                                    2131/711
CTC CCT GGA TCC TGA ACA AGG GCC CCA AAA GCA AGT TCT AAA GGG ACC CCT GAA ACC GAG
2161/721                                    2191/731
TAA GCC TTT GTG TCA AGA AGT GGG AGT ACA ACC AGA AAG GTG GCT GAG TGC TTT AGA G
```

Figure 12 (continuation 2)

mKOR

```
1/1                                    31/11
GCA CCT TGC TGA TCC CAA ACA GGC AGA GCT TCT TCC AGT CTT GGA AGG CAC AAA TTG AGC
61/21                                  91/31
ATC AGG AAC GTG GAC CCA TCA GGG CTG AAC AGC TAC TCA GGA TCT AAA GTG GTG ACT TGG
121/41                                 151/51
AAA GCT GAC GGT GAC TTG GGA AGG GAG GTC GCC AAT CAG CGA TCT GGA GCT GCA GCG CTC
181/61                                 211/71
ACC ATG GAG TCC CCC ATT CAG ATC TTC CGA GGA GAT CCA GGC CCT ACC TGC TCT CCC AGT
    met glu ser pro ile gln ile phe arg gly asp pro gly pro thr cys ser pro ser
241/81                                 271/91
GCT TGC CTT CTC CCC AAC AGC AGC TCT TGG TTC CCC AAC TGG GCA GAA TCC GAC AGT AAT
ala cys leu leu pro asn ser ser ser trp phe pro asn trp ala glu ser asp ser asn
301/101                                331/111
GGC AGT GTG GGC TCA GAG GAT CAG CAG CTG GAG TCC GCG CAC ATC TCT CCG GCC ATC CCT
gly ser val gly ser glu asp gln gln leu glu ser ala his ile ser pro ala ile pro
361/121                                391/131
GTT ATC ATC ACC GCT GTC TAC TCT GTG GTA TTT GTG GTG GGC TTA GTG GGC AAT TCT CTG
val ile ile thr ala val tyr ser val val phe val val gly leu val gly asn ser leu
421/141                                451/151
GTC ATG TTT GTC ATC ATC CGA TAC ACG AAG ATG AAG ACC GCA ACC AAC ATC TAC ATA TTT
val met phe val ile ile arg tyr thr lys met lys thr ala thr asn ile tyr ile phe
481/161                                511/171
AAC CTG GCT TTG GCA GAT GCT TTG GTT ACT ACC ACT ATG CCC TTT CAG AGT GCT GTC TAC
asn leu ala leu ala asp ala leu val thr thr thr met pro phe gln ser ala val tyr
541/181                                571/191
TTG ATG AAT TCT TGG CCT TTT GGA GAT GTG CTA TGC AAG ATT GTC ATT TCC ATT GAC TAC
leu met asn ser trp pro phe gly asp val leu cys lys ile val ile ser ile asp tyr
601/201                                631/211
TAC AAC ATG TTT ACC AGC ATA TTC ACC TTG ACC ATG ATG AGT GTG GAC CGC TAC ATT GCT
tyr asn met phe thr ser ile phe thr leu thr met met ser val asp arg tyr ile ala
661/221                                691/231
GTG TGC CAC CCT GTG AAA GCT TTG GAC TTC CGA ACA CCT TTG AAA GCA AAG ATC ATC AAC
val cys his pro val lys ala leu asp phe arg thr pro leu lys ala lys ile ile asn
721/241                                751/251
ATC TGC ATT TGG CTC CTG GCA TCA TCT GTT GGT ATA TCA GCG ATA GTC TTG GGA GGC ACC
ile cys ile trp leu leu ala ser ser val gly ile ser ala ile val leu gly gly thr
781/261                                811/271
AAA GTC AGG GAA GAT GTG GAT GTC ATT GAA TGC TCC TTG CAG TTT CCT GAT GAT GAA TAT
lys val arg glu asp val asp val ile glu cys ser leu gln phe pro asp asp glu tyr
841/281                                871/291
TCC TGG TGG GAT CTC TTC ATG AAG ATC TGT GTC TTC GTC TTT GCC TTT GTG ATC CCA GTC
ser trp trp asp leu phe met lys ile cys val phe val phe ala phe val ile pro val
901/301                                931/311
CTC ATC ATT ATT GTC TGC TAC ACC CTG ATG ATC CTG CGC CTG AAG AGT GTC CGG CTC CTG
leu ile ile ile val cys tyr thr leu met ile leu arg leu lys ser val arg leu leu
```

Figure 13

```
961/321                                    991/331
TCT GGC TCC CGA GAG AAG GAC CGA AAT CTC CGC CGC ATC ACC AAG CTG GTG CTG GTA GTA
ter gly ser arg glu lys asp arg asn leu arg arg ile thr lys leu val leu val val
  021/341                                  1051/351
GTT GCA GTC TTC ATC ATC TGT TGG ACC CCC ATT CAC ATC TTT ATC CTG GTG GAG GCT CTG
val ala val phe ile ile cys trp thr pro ile his ile phe ile leu val glu ala leu
1081/361                                   1111/371
GGA AGC ACC TCC CAC AGC ACA GCT GCC CTC TCC AGC TAT TAT TTC TGT ATT GCC TTG GGT
gly ser thr ser his ser thr ala ala leu ser ser tyr tyr phe cys ile ala leu gly
1141/381                                   1171/391
TAT ACC AAC AGC AGC CTG AAT CCT GTT CTC TAT GCC TTT CTG GAT GAA AAC TTC AAG CGG
tyr thr asn ser ser leu asn pro val leu tyr ala phe leu asp glu asn phe lys arg
1201/401                                   1231/411
TGT TTT AGG GAC TTC TGC TTC CCT ATT AAG ATG CGA ATG GAG CGC CAG AGC ACC AAT AGA
cys phe arg asp phe cys phe pro ile lys met arg met glu arg gln ser thr asn arg
1261/421                                   1291/431
GTT AGA AAC ACA GTT CAG GAT CCT GCT TCC ATG AGA GAT GTG GGA GGG ATG AAT AAG CCA
val arg asn thr val gln asp pro ala ser met arg asp val gly gly met asn lys pro
1321/441                                   1351/451
GTA TGA CTA GTC GTG GAA ATG TCT TCT TAT TGT TCT CCA GGT AGA GAA GAG TTC AAT GAT
val *                                      1381/461
CTT GGT TTA ACC CAG ATT ACA ACT GCA G
```

Figure 13 (continuation 1)

TRANSGENIC ANIMAL WHOSE EXPRESSION OF THE OPIATE RECEPTORS IS MODIFIED

The invention relates to a non-human transgenic animal in which the expression of at least one of the genes which code for opiate receptors is modified.

Opiates—the prototype of which is morphine—are the most potent analgesics available to medicine today. However, their use is limited by a range of secondary effects, including effects on autonomous functions (constipation, respiratory depression, hypotension, diuresis) and psychotropic effects.

The range of actions of opiates is mediated by membrane receptors of the nervous system, which recognize and specifically bind these compounds. 20 years ago, these receptors were discovered by pharmacological studies. Three receptors have been identified: mu, delta and kappa receptors. The genes which code for these three receptors have been cloned and complementary DNA nucleotide sequences which code for the 3 receptors are shown in FIG. 11 (mu), FIG. 12 (delta) and FIG. 13 (kappa). Selective ligands of the three classes of receptors exist at present, and study of the action of these compounds suggests:

that the mu receptor is the privileged target of the prototype opiate morphine, which is the analgesic used the most for treatment of severe pain, the mu receptor is also the main target of heroin, one of the most feared narcotics in the context of toxicomania, the delta receptor is also said to be involved in control of pain and the emotional state (well-being), but to a lesser degree, the kappa receptor, like the other two receptors, is said to play a role in the analgesic action of opiates. On the other hand, and in contrast to mu and delta, it is said to have a dysphorizing psychotropic action, an action which has been regarded as an advantage for the development of potent analgesics lacking a toxicomanogenic potential.

All the strategies devised in the last 20 years by the pharmaceuticals industries to develop an ideal analgesic are based on these pharmacological data. They comprise in vitro and in vivo analysis of the effect of opiate agonists or antagonists. The interpretation of the results is dependent on the mu/delta/kappa selectivity of the products studied and their pharmacokinetic properties for studies in vivo.

A range of pharmacological results seems to indicate the existence of several receptors in each of the classes mu, delta or kappa which could constitute distinct targets for the agonists of each of the classes of receptors. The question of whether only three receptors or several mu ($\mu$), delta ($\delta$) and kappa ($\kappa$) receptors exist has not been resolved at present.

Three genes which code for these receptors have been cloned very recently. Each of them corresponds to one of the above classes of receptors defined by pharmacology. Thus a mu gene, a delta gene and a kappa gene have been characterized at the molecular level. The involvement of these genes in the biological action of opiate substances in vivo has not been defined.

The genes which code for the opiate receptors have been cloned very recently (Kieffer B. (1995) Cellular and Molecular Neurobiology 15:615–635).

In the following, the gene of the $\mu$ receptor is called MOR, the gene of the $\delta$ receptor is called DOR and the gene of the $\kappa$ receptor is called KOR.

One of the objects of the invention is to provide an experimental model which enables targeting of medicaments which have potent analgesic properties without having the secondary effects of opiates of the morphine type.

One of the objects of the invention is to provide non-human transgenic mammalian animals in which at least one of the genes of the opiate receptors is no longer expressed.

One of the objects of the invention is to provide non-human transgenic mammalian animals in which the gene of the $\mu$ receptor is no longer expressed.

One of the objects of the invention is to provide non-human transgenic mammalian animals in which the gene of the $\delta$ receptor is no longer expressed.

One of the objects of the invention is to provide non-human transgenic mammalian animals in which the gene of the $\kappa$ receptor is no longer expressed.

One of the other objects of the invention is to provide an animal model which is capable of screening medicaments which act on pathologies involving at least one of the opiate receptors.

The invention relates to the use of a non-human transgenic mammalian animal in which the expression of at least one the genes which codes for the opiate receptors is modified, in particular suppressed in the tissues or cells of the brain, with respect to normal expression, in particular in the tissues or cells of the brain, for determination of a medicament which is active on pathologies involving the opiate receptors.

More precisely, the invention relates to the use of a non-human transgenic mammalian animal in which the expression of the gene which codes for an opiate receptor is modified, in particular in the nerve tissues, with respect to normal expression, in particular in the nerve tissues, for determination of a medicament which acts on pathologies involving the opiate receptors, in particular acute or chronic severe pain, toxicomania or the prevention or treatment of transplant rejections.

The term "mammalian" includes all mammals with the exception of humans, advantageously rodents, and in particular mice.

"Transgenic animal" is understood as meaning not only an animal in the genome of which an exogenous gene has been introduced, but also an animal in which expression of an endogenous gene has been deleted, either by interruption of the endogenous gene or by replacement of an endogenous gene or of a fragment thereof by a construction such that it no longer allows expression of the endogenous gene. Such animals will be called "knock-out" animals or those deficient in the said endogenous gene.

Normal expression of one of the opiate receptors can be defined by several methods:

1) Determination of the mRNA corresponding to one of the genes of the opiate receptors: this is possible by the technique of RNA transfer (Northern blot) in which the mRNAs are separated on denaturing agarose gel by electrophoresis; and the RNAs are then transferred and bound to a membrane of the nitrocellulose or nylon type. To reveal the presence of the RNAs corresponding to one of the genes of the opiate receptors, it is possible to use a probe corresponding to all or a fragment of the cDNA of the gene in question.

2) Determination of the amount of protein corresponding to one of the opiate receptors: this is possible by studying the bonding of an opiate ligand (agonist or antagonist), such as diprenorphin, which is non-selective with respect to opiate receptors, DAGO (selective with respect to $\mu$), naltrindole (selective with respect to $\delta$) and labelled CI977 (selective with respect to $\kappa$), to receptors present in a tissue (brain) homogenate. As regards the respective definitions of these ligands, these are shown in the legend of FIG. 2. In particular, the dissociation constant Kd of several specific ligands of one of the opiate receptors is known and is of the order of 1 nanomolar for the ligands generally used. It is furthermore known that the Bmax for the above ligands is of the order of 0.1 picomol/mg membrane protein for μ and δ receptors and 0.02 picomol/mg membrane protein for the κ receptor in respect of the mouse brain. It is thus known that a saturation curve with this ligand on membrane extracts containing the three opiate receptors prepared from the brain and analysis of the results obtained from the saturation curves by the Scatchard method (determination of the number of receptor sites) should give Bmax affinity values divided by two in heterozygotes and zero Bmax values (not measurable) in homozygotes.

This therefore allows quantification of the amount corresponding to one of the opiate receptors.

According to one embodiment, the invention relates to the use of a non-human transgenic mammalian animal which no longer expresses the gene of the μ receptor or of the κ receptor or of the δ receptor.

The modification and absence of expression of one of these genes can be determined in the following manner.

1) Mice where the gene of the opiate receptor has been modified such that it can no longer be expressed are first characterized in relation to the DNA by analysis by the DNA transfer method (Southern blot), with the aid of a probe consisting of a fragment containing all or some of the region of the opiate receptor, this probe being defined in the examples.

Hybridization of this probe clearly shows that the band corresponding to one of the opiate receptors of the wild type (that is to say normally present in animals) is no longer present in animals which are homozygous with respect to mutation, but is replaced by a band corresponding to the modified genome.

2) Analysis by RNA transfer (northern blot) of the RNA extracts of tissues which express one of the opiate receptors, in particular the brain, shows that there is no longer RNA expression corresponding to the wild gene. The probe used in this case is defined by the complementary DNA portion which codes for the μ opiate receptor of mice downstream of the unique BamHI site of the coding region up to the STOP codon.

3) Finally, it can also be demonstrated that the binding of specific ligands to one of the opiate receptors, in particular with the aid of the ligands DAGO (selective with respect to μ), naltrindole (selective with respect to δ) or CI977 (selective with respect to κ), is completely absent in these mice.

The tissues in which the expression of a gene which codes for an opiate receptor is modified are essentially the nerve tissues, and in particular the neuronal cells.

In the context of the invention, modification of the expression of the said gene in other types of cells, such as immune cells, is not excluded.

As regards the painful pathologies treated by the opiates to which the invention relates, there may be mentioned:

1. acute or chronic pain: pain due to excess nociception with tissue lesions, including cancer pain, postoperative pain, infectious pain and chronic pain of the inflammatory rheumatism and degenerative inflammatory rheumatism type, 2. chronic pain: pain due to lesion of the nervous system or neuropathic pain comprising (1) deafferentations (example: amputation) and deafferentations with nociception (example: postoperative residual lumbosciatalgia).

Furthermore, the opiate antagonists can have immunosuppressant properties which can be used to benefit in the prevention or treatment of transplant rejection, but the mechanism of this biological action is unknown.

In this respect, naltrindole has a suppressant effect on the mixed lymphocyte reaction (MLR) in vitro and prevents transplant rejection in vivo (Arakawa, K., Akami, T., Okamoto, M., Nakai, I., Oka, T., Nagase, H. Transplantation proceedings (1993) 25:738–740). Experimental protocols regarding the study of transplant rejection are to be found in this reference. The transgenic mice of the invention enable the mu component to be evaluated (verses delta and kappa) in the response of the mice to drugs under development, for example compounds derived from naltrindole (delta antagonists) for development of an agent which blocks transplant rejection.

It has furthermore been shown that opiate alkaloids have an immunosuppressant activity on other immune functions: they block/inhibit the production of antibodies and killer activity ("natural killers"), two essential components of immune responses against infections. Mice from which expression of opioid receptors has been deleted will therefore also be used as an animal model to test the action of immunosuppressant drugs of the opiate type developed for the above use for all the components of the immune response.

In the text above and below, "μ opiate receptor genes" are also understood as meaning the iso-forms generated by alternative splicing which are at the junction specific to the mu gene (between exon 3 and 4): Zimprich, A., Simon, T. and Höht, V. (1995) Cloning and expression of an isoform of the rat μ-opioid receptor (rMORIB) which differs in agonist-induced desensitizations from RMORI. FEBS 359:142–146 and Bare, L A., Mansson, E. and Yang, D M. (1994) Expressions of two variants of the human μ-opioid receptor mRNA in SK-N-SH cells and human brain. FEBS 354:213–216.

The invention also relates to the use of a non-human transgenic mammalian animal as described above which no longer expresses at least one of the following receptors: the opiate receptor of the mu type, the opiate receptor of the kappa type and the opiate receptor of the delta type.

The invention also relates to a non-human transgenic mammalian animal or mammalian cells containing the gene of the opiate receptor of the mu type in which a fragment of the gene of the receptor containing an exon, in particular exon 2, is either replaced by all or part of a marker gene under the control of a suitable promoter, or interrupted by the insertion between two contiguous nucleotides of all or part of a marker gene under the control of a suitable promoter, in particular the gene of resistance to neomycin (neo) under the control of the promoter phosphoglycerate kinase-1 (PGK-1), the expression of the gene of the mu type being suppressed.

According to an advantageous embodiment of the invention, the transgenic mammalian animal or the mammalian cells in which the μ gene is no longer expressed are such that they have an interruption in the μ for μδ and κ gene, in particular of an exon, and in particular exon 2, by the insertion between two contiguous nucleotides of all or part of a marker gene under the control of a suitable promoter, in particular the gene of resistance to neomycin (neo) under the control of the promoter phosphoglycerate kinase-1 (PGK-1), the expression of the gene of the mu type being suppressed.

The invention also relates to a non-human transgenic mammalian animal or mammalian cells containing the gene of the opiate receptor of the delta type in which a fragment of the gene of the receptor containing an exon, in particular exon 1, is either replaced by all or part of a marker gene under the control of a suitable promoter, or interrupted by the insertion between two contiguous nucleotides of all or part of a marker gene under the control of a suitable promoter, in particular the gene of resistance to neomycin (neo) under the control of the promoter phosphoglycerate kinase-1 (PGK-1), the expression of the gene of the delta type being suppressed.

According to an advantageous embodiment of the invention, the transgenic mammalian animal or the mammalian cells in which the delta gene is no longer expressed are such that there is replacement of a fragment of the δ gene containing an exon, in particular exon 1, by all or part of a marker gene under the control of a suitable promoter.

The invention also relates to a non-human transgenic mammalian animal or mammalian cells containing the gene of the opiate receptor of the kappa type in which a fragment of the gene of the receptor containing an exon, in particular exon 1, is either replaced by all or part of a marker gene under the control of a suitable promoter, or interrupted by the insertion between two contiguous nucleotides of all or part of a marker gene under the control of a suitable promoter, in particular the gene of resistance to neomycin (neo) under the control of the promoter phosphoglycerate kinase-1 (PGK-1), the expression of the kappa gene being suppressed.

According to an advantageous embodiment of the invention, the transgenic mammalian animal or the mammalian cells in which the kappa gene is no longer expressed are such that there is replacement of a fragment of the κ gene containing an exon, in particular exon 1, by all or part of a marker gene under the control of a suitable promoter.

The invention also relates to cells cultured from non-human transgenic mammalian animals described above.

According to an advantageous embodiment, the invention relates to cell cultures containing one of the said transgenic constructions.

These cell cultures can be obtained either from cells taken from transgenic animals as defined above or from cell lines using the said transgenic constructions, where this second possibility can be carried out with the aid of standard techniques of cell transfection.

The invention also relates to a non-human transgenic mammal as is obtained by introduction into a blastocyte of embryonal strain cells (ES cells) comprising, in their genome, one of the said transgenic constructions obtained by homologous recombination, selection of chimaeric male animals according to a criterion corresponding to the ES line; crossing of the animals selected with mice, in particular C57 Black 6 mice, to obtain animals which are heterozygous with respect to one of the said constructions, and where appropriate crossing of two heterozygotes to obtain an animal which is homozygous with respect to one of the said constructions.

The homozygote has a 129/C57 Black 6 50/50 genetic base. It is possible to return to a C57 Black 6 genetic base by homozygous crossing with C57 Black 6 mice over at least 12 generations.

C57 Black 6 mice are advantageously chosen since this genetic base is more favourable for certain behaviour experiments.

The invention also relates to a transgenic mammal as produced by crossing transgenic animals which express one of the transgenic constructions defined above.

The invention also relates to a process for obtaining a transgenic model for studying pathologies involving the opiate receptors of the mu type or the opiate receptors of the delta type or the opiate receptors of the kappa type and their treatment, comprising replacement of the endogenous gene of the opiate receptor of the μ type or of the endogenous gene of the opiate receptor delta type or of the endogenous gene of the opiate receptor of the kappa type in cells, in particular embryonal strain (ES) cells of mice, by a construction comprising the gene of the opiate receptor of the mu type or the gene of the opiate receptor of the delta type or the gene of the opiate receptor of the kappa type in which, respectively, exon 2 of the gene of the opiate receptor of the mu type is interrupted between two contiguous nucleotides by a portion of a marker gene under the control of a suitable promoter, in particular a cassette containing the neo gene under the control of the promoter PGKI or a fragment containing exon 1 of the gene of the opiate receptor of the delta type is replaced by a marker gene under the control of a suitable promoter, in particular a cassette containing the neo gene under the control of the promoter PGKI, or a fragment containing exon 1 of the gene of the opiate receptor of the kappa type is replaced by a marker gene under the control of a suitable promoter, in particular a cassette containing the neo gene under the control of the promoter PGKI, and in particular in which the gene of the opiate receptor of the mu type is interrupted at the BamHI site of exon 2 by insertion of the cassette PGK-neo, or the genomic fragment SmaI—SmaI of 600 bp containing exon 1 of the gene of the opiate receptor of the delta type is replaced by the cassette PGK-neo, or the genomic fragment of 235 bp of exon 1 of the gene of the opiate receptor of the kappa type containing the ATG initiator of exon 1 and 232 base pairs downstream of the said ATG is replaced by the cassette PGK-neo, and introduction of the said cells into embryos, in particular blastocytes of non-human mammals, selection of male chimaeric animals according to a criterion corresponding to the ES line, crossing of the animals selected with mice, in particular C57BL/6 mice, to obtain animals which are heterozygous with respect to one of the constructions according to the invention and where appropriate crossing of two heterozygotes to obtain an animal which is homozygous with respect to one of the constructions according to the invention.

The criterion used is, for example, the color of the hair (agouti).

The invention relates to a process for screening medicaments which act on pathologies involving opiate receptors, in particular the following pathologies: acute or chronic severe pain, toxicomania and prevention or treatment of transplant rejection, comprising:

administration to a transgenic non-human mammal or transgenic non-human mammalian cells containing, instead of the endogenous gene of the opiate receptor of the mu type, or the endogenous gene of the opiate receptor of the delta type, or the endogenous gene of the opiate receptor of the kappa type, a construction containing the gene of the opiate receptor of the mu type, or the gene of the opiate receptor of the delta type, or the gene of the opiate receptor of the kappa type in which, respectively, exon 2 of the gene of the opiate receptor of the mu type is interrupted between two contiguous nucleotides by a portion of a marker gene under the control of a suitable promoter, in particular a cassette containing the neo gene under the control of the promoter PGKI or a fragment containing exon 1 of the gene of the opiate receptor of the delta type is replaced by a marker gene under the control of a suitable promoter, in particular a cassette containing the neo gene under the control of the promoter PGKI, or a fragment containing exon 1 of the gene of the opiate receptor of the kappa type is replaced by a marker gene under the control of a suitable promoter, in particular a cassette containing the neo gene under the control of the promoter PGKI, and in particular in which the gene of the opiate receptor of the mu type is interrupted at the BamHI site of exon 2 by insertion of the cassette PGK-neo, or the genomic fragment SmaI—SmaI of 600 bp, containing exon 1 of the gene of the opiate receptor of the delta type is replaced by the cassette neo, or the genomic fragment of 235 bp of exon 1 of the gene of the opiate receptor of the kappa type containing the ATG initiator of exon 1 and 232 base pairs downstream of the said ATG is replaced by the cassette PGK-neo;

determination of the nociceptive thresholds by the tail immersion and hot plate test after injection of the drugs to be tested, determination of the response to drugs to be tested by animals in which has been produced chronic pain induced by injection of irritating products, carrageenan and Freund's adjuvant, and producing monoarthritis or polyarthritis, or the test of sciatic nerve section, or the test of sciatic nerve ligation in the case of neuropathic pain, or determination of the psychotropic properties of drugs to be tested by the tests of preference of position or of auto-administration, or determination of the level of physical dependence by induction of severe dependence and provocation of withdrawal in the case of toxicomania, or determination of the mixed lymphocyte reaction and of the life of transplants (Arakawa, K., Akami, T., Okamoto, M., Nakai, I., Oka, T., Nagase, H. Transplantation proceedings (1993) 25:73 8–740) in the case of prevention or treatment of transplant rejection.

The invention also relates to a transgenic construction containing the gene of the opiate receptor of the mu type, or the gene of the opiate receptor of the delta type, or the gene of the opiate receptor of the kappa type in which, respectively, exon 2 of the gene of the opiate receptor of the mu type is interrupted between two contiguous nucleotides by a portion of a marker gene under the control of a suitable promoter, in particular a cassette containing the neo gene under the control of the promoter PGKI or a fragment containing exon 1 of the gene of the opiate receptor of the delta type is replaced by a marker gene under the control of a suitable promoter, in particular a cassette containing the neo gene under the control of the promoter PGKI, or a fragment containing exon 1 of the gene of the opiate receptor of the kappa type is replaced by a marker gene under the control of a suitable promoter, in particular a cassette containing the neo gene under the control of the promoter PGKI, and in particular in which the gene of the opiate receptor of the mu type is interrupted at the BamHI site of exon 2 by insertion of the cassette neo, or the genomic fragment SmaI—SmaI of 600 bp containing exon 1 of the gene of the opiate receptor of the delta type is replaced by the cassette PGK-neo, or the genomic fragment of 235 bp of exon 1 of the gene of the opiate receptor of the kappa type containing the ATG initiator of exon 1 and 232 base pairs downstream of the said ATG is replaced by the cassette PGK-neo.

DESCRIPTION OF THE FIGURES

FIG. 1:

Figure 2A:
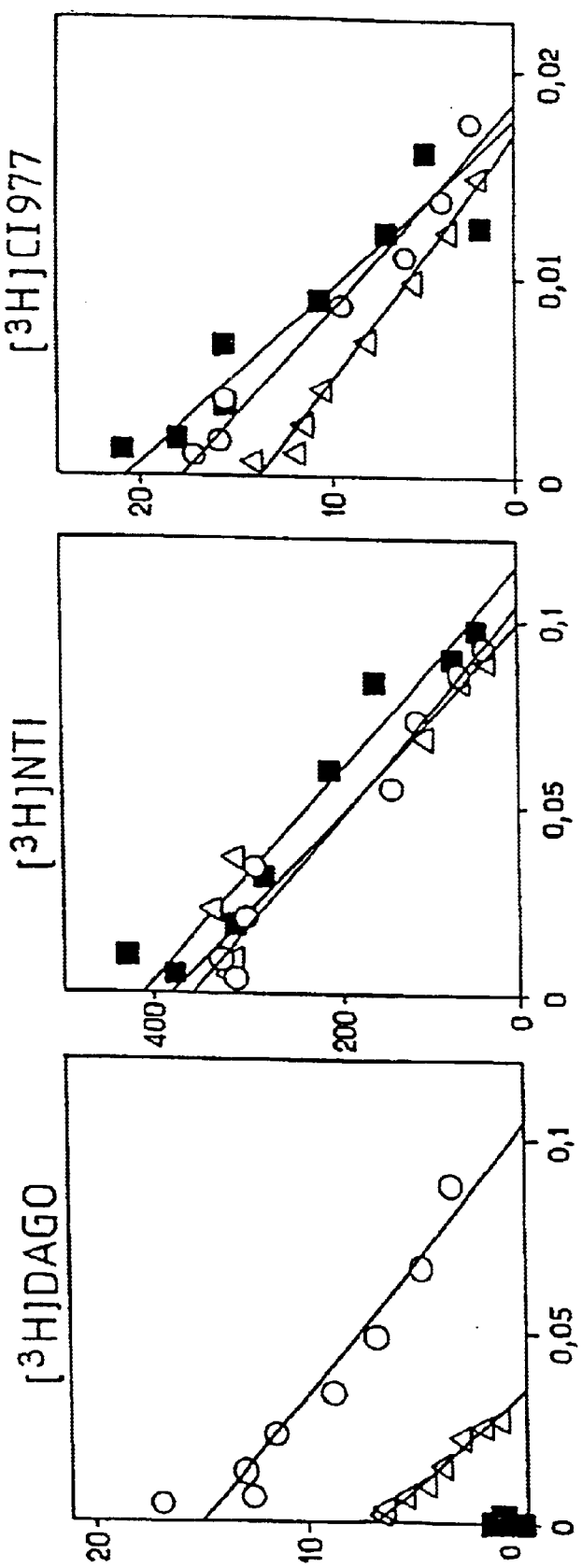

Interruption of the gene of the $\mu$ opioid receptor.

a) Strategy for preparation of mice which no longer express the $\mu$ gene. The genomic organization and the restriction maps are shown in the following manner: for the construction (top), wild gene (middle) and recombinant gene (bottom). The black boxes represent the coding regions and the white box represents the Neo gene. The bold line indicates the probe at 5' used to identify the homologous recombination events. E=exon; Neo=gene of resistance to neomycin; restriction sites: B=BamHI; S=SalI: Sp=SpeI.

b) Genomic analysis by DNA transfer (Southern blot) carried out with DNA digested by BamHI from electroporated ES cells using the 5' probe. The fragments of the wild gene and of the recombinant gene are 6.3 kb and 7.6 kb respectively.

c) Genomic analysis by DNA transfer (Southern blot) carried out with DNA of the tails of mice. The heterozygous mice are crossed and the genomic DNA of their offspring is subjected to BamHI digestion and analysed using the 5' probe. The genotypes are described above each band: +/+= wild; +/–=heterozygous; –/–=homozygous.

FIG. 2:

FIG. 2:

Analysis of binding sites of the $\mu$, $\delta$ and $\kappa$ receptors in the brains of wild +/+, heterozygous +/– and homozygous –/– mice deficient in the gene of the $\mu$ receptor.

a) A Scatchard analysis with respect to binding with [3H] DAGO ($\mu$), [3H] NTI ($\delta$) and [3H] CI977 ($\kappa$) is shown for each genotype of mice. A representative test is shown. The Bmax and Kd values (±SD=standard deviation) from at least three separate experiments are indicated.

|  | Kd | Bmax | Kd | Bmax | Kd | Bmax |
|---|---|---|---|---|---|---|
| O +/+ | 1.343 | 0.099 | 0.068 | 0.095 | 0.214 | 0.019 |
|  | (0.104) | (0.005) | (0.005) | (0.010) | (0.019) | (0.001) |
| Δ +/– | 1.133 | 0.040 | 0.075 | 0.103 | 0.198 | 0.021 |
|  | (0.105) | (0.004) | (0.011) | (0.010) | (0.025) | (0.003) |
| ■ –/– | und | und | 0.082 | 0.124 | 0.211 | 0.022 |
|  |  |  | (0.014) | (0.008) | (0.025) | (0.002) | und = undetectable b) Computerized colored autoradiograms of coronary sections of the brains of mice cut at the caudate putamen. The top panels show the $\mu$ receptors labelled with [3H] DAGO, the middle panels show the $\delta$ receptors labelled with [3H] DELTI and the lower panels show the $\kappa$ receptors labelled with [3H] CI977. The binding is expressed in fmol/mg of tissue section and the specific binding is >85% for the $\mu$ and $\delta$ labelling and >75% for the $\kappa$ labelling. The wild, heterozygous and homozygous mice are treated in parallel for the binding and for the development of the autoradiograms.

c) As in b), except that the coronary sections are shown at the hippocampus.

Methods

To analyse the saturation, the binding is carried out using membrane proteins of the whole brain (Ilien et al. Biochemical Pharmacology (1988). 37:3843–3851) in an amount of 100 µg incubated in Tris-HCl 50 mM pH 7.4, EDTA 1 mM 25° C. for 1 h with [$^3$H] DAGO (Amersham), [$^3$H] NTI (donated by A. Borsodi) or [$^3$H] C.1977 (Amersham) using concentration ranges of 0.05–6.4 nM, 0.005–0/64 nM and 0.01–1.28 nM respectively. Naloxone (Sigma) is used in a concentration of 2 µM to determine the non-specific binding. The experiments are carried out in triplicate using at least two separate membrane preparations, each produced from three brains. The binding data are analysed using the EBDA-ligand program (Biosoft). For the mapping by autoradiography, the mice are sacrificed by decapitation and the intact brains removed and frozen immediately in isopentane at −20° C. Frozen coronary sections of 20 µm are cut in a cryostat (Zeiss Microm 505E) and are mounted during thawing on microscope slides pretreated with gelatine and dried using anhydrous $CaSO_4$ for 1 week at −20° C. An additional group of sections is cut adjacent to those for the determination of non-specific binding, which is carried out with naloxone for all the ligands (1 µM for DAGO, CI-977 and 10 µM for DELT I). The slides are preincubated in Tris-HCl 50 mM, pH 7.4 plus 0.9% NaCl for 30 minutes to removed endogenous opioids. A concentration of about 3 to 4 times the Kd is used for labelling the receptors ([$^3$H] DAGO, 4 nM; [$^3$H] DELT I, 7 nM; [$^3$H] CI1977, 2.5 nM). Binding is carried out in Tris-HCl 50 mM, pH 7.4 (1 ml for each slide) at room temperature for 60 minutes for all the ligands, and the samples are washed three times with Tris-HCl buffer cooled to 4° C. (5 minutes), dried rapidly in fresh air and desiccated for 3 days before placing on [−$^3$H]-Hyperfilm (Amersham) autoradiography films for a period of three weeks (µ and δ) and four weeks. All the slides of the +/+, +/− and −/− brains are deposited on the same film, developed (using 50% Kodak D19 developer, 3 minutes) and analysed using an MCID image analyser (Imaging Research, Canada). Ligands: CI977 (enadolin or (−)-5b,7b, 8a)-3,4-dichloro-N-methyl-N-[7-(1-pyrrolidinyl)-1-oxaspiro[4,5]-dec-8-yl]benzo[b]furan-4-acetamide), DAGO, [$^3$H]-D-Ala$^2$MePhe$^4$Gly-ol$^5$ enkephalin; DELT I, D-Ala$^2$deltorphin I; NTI, naltrindole.

FIG. 3:

Analysis of the in situ hybridization of genes of endogenous opioid peptides in mutant and wild brains.

a) Coronary sections at the striatum (PENK and PDYN, magnification×15) and at the hypothalamus (POMC, magnification×40) of +/+, +/− and −/− brains are shown under illumination in a dark field with the grain of the signal appearing in white. Labelling using antisense RNA probes of proenkephalin (PENK) and prodynorphin (PDYN) is detected in the accumbens (ACB) nucleus, caudate putamen (CPU), olfactory tubercule (OTU) and piriform cortex (PIR) and the labelling using the antisense ribo-probe POMC is detected in the arcuate nucleus (AN).

b) The high magnification (×100) of sections through the hypothalamus and through the pituitary gland of the brains of +/+and −/− mice hybridized with the antisense ribo-probe proopiomelanocortin (POMC) is photographed under illumination in a bright field (the grains of the signal appear as black spots). The cells containing the transcript POMC are shown in the arcuate nucleus and the labelling of the intermediate lobe (IL) of the pituitary glad is also shown.

Methods

Sections (10 µM) are prepared in a cryostat from frozen brains and hybridized with specific antisense ribo-probes labelled with $^{35}$S as described (Decimo et al., (1995) In situ hybridization of nucleic acid probes to cellular RNA. In Gene Probes 2, A practical approach, Ed. Hames B. D. et Hiddins S., 183–210 Oxford University Press, Oxford). The probe PENK is synthesized from a fragment of cDNA of 800 bp PvuII-XbaI cloned in pBluescript, the probe PDYN is synthesized from a restriction fragment of 1,700 bp PstI-EcoRI sub-cloned in pSP64, and the probe POMC is synthesized from a fragment of 400 bp NotI-NcoI cloned in pBluescript. The cDNAs are donated by E. Borrelli. The ribo-probes are synthesized in parallel, the brains of the three genotypes are treated and hybridized in the same series of experiments and exposed to Kodak NTB-2 emulsion for the same period of time.

FIG. 4:

Spontaneous locomotor activity of mutant mice deficient in µ opioid receptors (−/−) and their wild-type congeners (+/+). The boxes consist of plastic rectangular areas (25.5 cm×20.5 cm) with two crossed photocells isolated in a sound-proof frame with weak illumination (lux). The locomotor activity is measured at 1400 h for three consecutive days. The measurement lasts 15 minutes. On days 5 and 6, the locomotor activity is recorded at 1400 h and 0200 h respectively. All the experiments are carried out by a blind observer. The values are analysed by the ANOVA statistics system. The individual comparisons are made by the Dunnett test. Number of animals: 24 wild and 23 mutant. The black squares correspond to homozygous mice and the white squares correspond to wild mice. The black stars indicate the comparison at different measurement times for the same group of animals:

a. left-hand graph: between the first and third day, b. right-hand graph: between 1400 h and 0200 h.

The white stars show the comparison between the wild and mutant groups at the same measurement time (bilateral Dunnett test).

One star corresponds to p <0.05 and two stars correspond to p <0.01.

FIG. 5:

Antinociceptive responses to the administration of morphine in mutant mice deficient in the µ opioid receptor (−/−) and their wild-type congeners (+/+). To evaluate the response to pain, the following were carried out:

a) tail immersion test;

b) hot plate test.

The tail immersion test (54° C.) and hot plate test are carried out 10 minutes and 20 minutes respectively after injection of saline solution or morphine. The maximum time observed is 15 seconds for the tail immersion test and 30 and 180 seconds respectively for the licking and jumping response in the hot plate test. The pharmacological tests and the care of the animals are undertaken in accordance with standard ethical standards (NIH, 1985). The values are analysed by ANOVA (mutation and treatment) between the subjects. The individual comparisons are made by the Dunnett test. The number of animals per group is 7 to 11.

The black squares correspond to homozygous mice and the white squares correspond to wild mice.

The black stars indicate the comparisons between the animals treated with a saline solution (control animals) of the same genotype and the white stars show the comparison between the wild and mutant groups which receive the same treatment (bilateral Dunnett test).

One star corresponds to p <0.05 and two stars correspond to p <0.01.

FIG. 6:

To evaluate the euphorizing character of drugs, the test of position of preference at the conditioned position, induced by morphine in mice deficient in the μ opioid receptor (−/−) and their wild-type congeners (+/+), is carried out. The paradigm of the preference of position is effected using the same experimental conditions as those given in (Valverde et al., 1996), with the exception of the conditioning time (18 minutes) and the size of the compartments (15 cm×15 cm×15 cm). In brief, the conditioning plan consists of 3 phases. During the preconditioning phase, the animals are placed on a neutral surface and the time spent in each compartment is recorded. The conditioning phase consists of 6 consecutive days of morphine (3 mg/kg, subcutaneous) or saline solution. The doors situated on the walls of the compartments allow the mice to be confined immediately after the injection. The mice receive the morphine on days 1, 3 and 5 and the saline solution on days 2, 4 and 6. The control animals receive the saline solution each day. The test phase is carried out exactly as the preconditioning phase (free access to each compartment), 24 h after the final conditioning stage. The data are expressed in results calculated as the difference between the postconditioning and preconditioning time spent in the compartment associated with the medicament. The values are analysed by ANOVA (mutation and treatment) between the subjects. The number of animals per group is 9 to 14.

The black stars indicate the comparisons between the animals treated with a saline solution (control animals) of the same genotype and the white stars show the comparison between the wild and mutant groups which receive the same treatment (bilateral Student "t test).

Two stars correspond to p <0.01.

FIG. 7:

Incidence of abstinence measured during the morphine deficiency syndrome caused by naloxone in mutant mice deficient in μ opioid receptors (−/−) and their wild-type congeners (+/+).

a) Somatic symptoms. The black squares correspond to homozygous mice and the white squares correspond to wild mice.

b) Vegetative symptoms.

The results are expressed as means ±SD. The dependence on opiates is induced in the mice by repeated intraperitoneal injections of morphine at intervals of 12 hours for 6 days. The dose of morphine is increased progressively as follows: first day, 20 mg/kg; second day: 40 mg/kg; third day: 60 mg/kg; fourth day: 80 mg/kg; fifth day: 100 mg/kg; sixth day (only one injection in the morning): 100 mg/kg. The control mice are treated with saline solution under the same conditions. The deficiency is caused in each animal by injecting naloxone (1 mg/kg, subcutaneous) only once 2 hours after the last administration of morphine. Thirty minutes before the injection of naloxone, the animals are placed individually in test chambers consisting of transparent circular boxes (30 cm diameter×50 cm height) with a white floor. During the 15 minutes preceding the injection of naloxone, the mice are observed in order to verify the presence of normal behaviour. The somatic symptoms of deficiency are evaluated immediately after injection of the opiate antagonist for a period of 30 minutes. The number of shakings, jumps, tremors of the paw and sniffing are counted. The chattering of teeth, diarrhoea, tremors and ptosis are evaluated for periods of 5 minutes, a point for the presence of each symptom being given for each period. The number of periods showing the symptom is then counted (maximum score: 6). The body weight and the rectal temperature are determined 2 minutes before and 30 minutes after the injection of naloxone. The rectal temperature is also measured 60 minutes after the naloxone. See the legend to FIG. 5 for the statistical analysis. The number of animals per group ranges from 9 to 14.

The black squares correspond to homozygous controls which received an injection of saline solution. The white squares correspond to wild controls which received an injection of saline solution.

The squares with close diagonal lines correspond to homozygous controls which received an injection of morphine. The squares with spaced diagonal lines correspond to wild controls which received an injection of morphine.

The black stars indicate the comparisons between the animals treated with a saline solution (control animals) of the same genotype and the white stars show the comparison between the wild and mutant groups which receive the same treatment (bilateral Student "t test).

One star corresponds to p <0.05 and two stars correspond to p <0.01.

FIG. 8: ES screening: Interruption of the mu gene by homologous recombination:

A. Representation of a BamHI—BamHI fragment (about 14 kb) of the mu gene of mice for which homologous recombination has taken place. The neo gene with its promoter and its polyadenylation signal are inserted into exon 2 (nucleotides 6375 to 7989). The position of the external probes 5' and 3' and the neo probe are indicated in bold under the diagram of the gene fragment.

B. Size of fragments expected during Southern screening of the genomic DNA of ES cells. Digestion of the DNA by BamHI and Southern hybridization with probe I (=5' probe). WT=wild fragment; Rec=mutated fragment.

C. Size of the fragments expected during Southern screening of the genomic DNA of ES cells. Digestion of the DNA by BamHI and Southern hybridization with probe II (=neo probe). WT=wild fragment; Rec=mutated fragment.

D. Size of the fragments expected during Southern screening of the genomic DNA of ES cells. Digestion of the DNA by EcoRI+NcoI and Southern hybridization with probe III (=3' probe). WT=wild fragment; Rec=mutated fragment.

Legend:

the track corresponds to the genome, the white rectangle corresponds to the mMOR intron, the black rectangle corresponds to the mMOR exon, the rectangle with spaced diagonal lines corresponds to the promoter PGK, the rectangle with close diagonal lines corresponds to the neo gene.

FIG. 9: δ construction

Interruption of the delta gene by homologous recombination.

A. Restriction map of a fragment of SacI-EcoRI of about 14.5 kb of the delta gene of mice containing exon 1 which codes for amino acids 1 to 77 of the delta receptor.

B. Portion of the delta gene SacI-EcoRI used to realize the homologous recombination vector. The fragment of 1.9 kb containing the neo gene has been inserted into the SmaI sites present on either side of exon 1.

C. Result of homologous recombination: all of exon 1 is replaced by the neo gene. The position of the external probes 5' and 3' used for screening is indicated in the form of bold tracks under the diagram of the gene fragment. The 5' probe (=probe 1) corresponds to a SacI—SacI fragment of 700 bp. The 3' probe (=probe 2) was obtained by PCR with the oligo-components indicated on the diagram and has a size of 300 bp.

Legend:

the squares with diagonal lines correspond to the neo gene, the squares with lozenges correspond to exon 1.

| A = ApaI | S = SacI |
|---|---|
| B = BamHI | Sal = SalI |
| E = EcoRI | Sc = ScaI |
| K = KpnI | Sm = SmaI |
| N = NotI | Sp = SpeI |

FIG. 10: κ construction:

Interruption of the kappa gene by homologous recombination.

A. Restriction map of an EcoRI—EcoRI fragment of about 16 kb of the kappa gene of mice containing exons 1 and 2 which code respectively for amino acids 1 to 86 and 87 to 102 of the kappa receptor. The EcoRI, SacI and BamHI sites are naturally present in the gene. The two SmaI sites were created by directed mutagenesis. The sizes of the BamHI—BamHI and EcoRI—EcoRI fragments are indicated.

B. BamHI—BamHI portion of the kappa gene used to realize the homologous recombination vector.

C. Result of the homologous recombination: the majority of exon 1 is replaced by the neo gene. The position of the external probes 5' and 3' used for the screening is indicated in the form of bold tracks under the diagram of the gene fragment.

FIG. 11:

FIG. 11 shows the nucleotide sequence and the amino acid sequence deduced from the gene which codes for the mu receptor of mice, flanked by non-translated 5' and 3' nucleotide sequences.

FIG. 12:

FIG. 12 shows the nucleotide sequence and the amino acid sequence deduced from the gene which codes for the delta receptor of mice, flanked by non-translated 5' and 3' nucleotide sequences.

FIG. 13:

FIG. 13 shows the nucleotide sequence and the amino acid sequence deduced from the gene which codes for the kappa receptor of mice, flanked by non-translated 5' and 3' nucleotide sequences.

EXAMPLE 1

Creation of a Line of Mutant Mice for Which the Gene Which Codes for the mu Opioid Receptor is no Longer Expressed Methods. A genomic bank of mice derived from the strain 129/sv is screened using a cDNA probe of the δ opioid receptor of mice (Kieffer B. et al., (1992) PNAS 89:12048) under weakly stringent conditions. A genomic fragment which codes for the μ receptor containing exons 2 and 3 is obtained, and an SalI/SpeI fragment of 6.8 kb is excised and sub-cloned in pBlueScript (Stratagene). A BglII cassette of 1.6 kb containing the gene of resistance to neomycin under the control of the promoter PGK (Lufkin, T., Dierich, A., LeMeur, M., Mark, M and Chambon, P. (1991) Cell 66:1105) is inserted into a unique BamHI site present in exon 2, thus eliminating endogenous BamHI sites and interrupting the sequence which codes at the level of the second intracellular loop (amino acid 193). The target vector is linearized and electroporated in (P1)-ES cells (Lufkin, T., Dierich, A., LeMeur, M., Mark, M and Chambon, P. (1991) Cell 66:1105). The clones resistant to neomycin are screened by DNA transfer using a 5' probe labelled with $^{32}$P generated by PCR on genomic fragments originating from the digestion by BamHI. The same transfers are then hybridized with a 3' probe generated by PCR, as well as the Neo probe made up of the BamHI-PvuII fragment of 536 bp of the cDNA which codes for neomycin (Lufkin, T., Dierich, A., LeMeur, M., Mark, M and Chambon, P. (1991) Cell 66:1105) to confirm homologous recombination.

As regards the probes, these were generated by PCR from the genomic DNA in the region situated between the BamHI and SalI sites for the 5' probe and close to the NcoI site for the 3' probe. The oligonucleotides which have enabled them to be obtained are the following:

5' probe: sense oligo: 5' CTGGATAATAATGGAGAAATA-CAGAC3' antisense oligo: 5' AGAGGGAGCCTGTAAGCAT-GAAG3'

Size: 463 bp

3' probe: sense oligo: 5' TGTGGCTCCGCAGGT-TCTAGCA3' antisense oligo: 5' TGCACTTGACAACACA-GAGTTTA3'

Size: 1,010 bp.

A positive clone is micro-injected into C57BL/6 blastocytes (Lufkin, T., Dierich, A., LeMeur, M., Mark, M and Chambon, P. (1991) Cell 66:1105) and gives birth to chimaeric descendants, which in their turn are crossed with C57BL/6 mice. The agouti-colored young mice are karyotyped by analysis by DNA transfer of a biopsy of the tails and the males transmitting the line are used to found a colony.

Result: Generation of mice deficient in MOR.

The gene of the μ opioid receptor (MOR) is inactivated in 129/Sv embryonal strain cells by insertion of a Neo cassette into the coding region of the gene (FIG. 1a). The targeting events of the gene are identified by DNA transfer (FIG. 1b) and 7 clones among 90 resistant to neomycin are found to be positive, representing a targeting frequency of $\frac{1}{13}$. Analysis by DNA transfer using a 3' probe generated by PCR and the Neo probe confirms the precise integration of a unique copy of the fragment of the interrupted MOR gene (not shown). An ES positive clone is used to establish a mutant mouse (FIG. 1c). Analysis by saturation of the binding of (3H) DAGO ([$^3$H]-D-Ala$^2$-MePhe$^4$Gly-ol$^5$) to homogenates of whole brains confirms a reduction of 50% in the binding sites of the μ receptor in the heterozygous animals and a total loss of the binding of the μ ligand in the homozygous mutants (FIG. 2a). The autoradiography studies of the (3H) DAGO binding show the absence of the binding site of the μ receptor in all the sections of brain examined in the homozygous mice and a reduction by half in the heterozygous mice. These results demonstrate the complete inactivation of the MOR gene.

Results

The genotype of mice shows that the heterozygous descendants follow the expected Mendel frequency, indicating the absence of mortality in utero of animals deficient in the MOR gene on the two alleles. No obvious morphological anomaly could be detected in the homozygous mutant mice and the general anatomy of their brain appears normal, suggesting the absence of major involvement of the MOR gene in development. Mice deficient in the MOR gene do not differ from their congeners in health and growth. The homozygous mice are fertile, are raised normally and no incidence of maternal behaviour was to be observed.

Expression of Endogenous Opioid Peptides and Binding Sites of the Opioid Receptor To determine whether the absence of the $\mu$ receptor may alter expression of the $\delta$ and $\kappa$ receptors, the number of binding sites of $\delta$ and $\kappa$ receptors on homogenates of the whole brain was quantified. Analysis by the Scatchard test using specific radiolabelled ligands of $\delta$ (NTI) and $\kappa$ (CI977) show binding curves which are superimposable for the brains of +/+, +/− and −/− mice (FIG. 2a), and Kd and Bmax values (number of receptor sites) which agree with those reported in the literature (Boyle S. J. et al., (1990) Molecular Neuropharmacology 1:23–29; Fang R. J. et al., (1994) Journal of Pharmacol. Exp. Therapeutics 268:836–846 and Robson L. E. et al., (1985) European Journal of Pharmacol. 112:65–71). These results show that the total number of $\delta$ and $\kappa$ receptors is not modified in the animals deficient in the $\mu$ receptor. Given that the distribution of receptors may nevertheless be modified, complete autoradiography mapping was carried out on the olfactory bulb in the frontal and median regions of the brain. In the wild-type mice, the anatomical distribution of the $\mu$, $\delta$ and $\kappa$ sites is similar to that reported in other mice (Moskowitz and Goodman, 1985; Dupin et al., 1991; Sharif and Hughes, 1989) and the rat (Mansour et al., 1987; Boyle et al., 1990). Binding to the $\delta$ and $\kappa$ receptors is present in all the regions in which binding is detected in the wild-type mice. However, there are a few quantitative differences in the region and a lower number of receptors was detected by deltorphin 1 in the −/− mouse. It was also determined whether this difference is due to the method or genuine.

Three precursors of opioid peptides have been described in the central nervous system, proenkephalin (PENK), pro-dynorphin (PDYN) and proopioimelanocortin (POMC). The synthesis of POMC is reduced at the arcuate nucleus of the hypothalamus in the brain, while the PENK and PDYN transcripts have distributions which substantially overlap in the basal ganglia (Kachaturian et al., (1993) Handbook of Exp. Pharmacol. vol. 104/I, Opioids I. ed. A. Herz). The effect of the absence of the $\mu$ receptor on expression of these genes was investigated using analysis by hybridization in situ. There was no modification in the expression network of PENK in the olfactory tubercule, the piriform cortex, the accumbens nucleus and the striatum among the genotypes of mice (FIG. 3a). In the basal ganglia, the mRNA of PDYN is found to be increased in the accumbens and is less abundant in the caudate putamen for the three mice brains +/+, +/− and −/− (FIG. 3a). Furthermore, radiolabelling of the supraoptic and paraventricular hypothalamic nuclei by the PDYN probe is unchanged (not shown), and the expression of POMC is limited to arcuate neurons in the three strains of mice (FIG. 3a), with a similar number and distribution of cells containing the transcript (FIG. 3b), Finally, the expression of POMC is also investigated in the pituitary gland, and high labelling of the intermediate lobe is found, with no significant difference in the animals deficient in the $\mu$ receptor (FIG. 3b). Consequently, the labelling diagrams look indistinguishable among the genotypes, suggesting that the levels of distribution and expression of opioid peptides are unchanged in the absence of $\mu$ receptors.

PMOC and PENK code for beta-endorphins and enkephalins, peptides which preferably target the $\mu$ receptor. The absence of an obvious reduction in these peptides in the absence of their receptor suggests that the expression of the receptor does not exert a negative control on the synthesis of endogenous ligands.

Spontaneous Behaviour

The spontaneous locomotor activity of mutant mice is evaluated in locomotor activity boxes during three sessions carried out at 1400 hours on consecutive days. When the animals are exposed to the boxes for the first time, no significant difference in locomotor activity is observed between the mutant mice and their wild-type congeners. However, a tendency towards hypolocomotion is observed in the first two sessions. The locomotor activity of the mice is then measured in the same boxes during the day (1400 hours) and the night 0200 hours). Both the mutant mice and the wild-type mice show a significant increase in locomotor activity during the night, suggesting that the circadian rhythm is not modified in the mice which lack the $\mu$ receptor. During the periods of day and night, the activity of the mutant animals is also lower in this familiar environment, according to a preliminary observation made during the first two sessions. The locomotor activity in animals which are deficient in the $\mu$ receptor and are homozygous is thus decreased slightly (22% of the degree of wild mice).

Response to Acute and Chronic Treatment with Morphine

Figure 5:
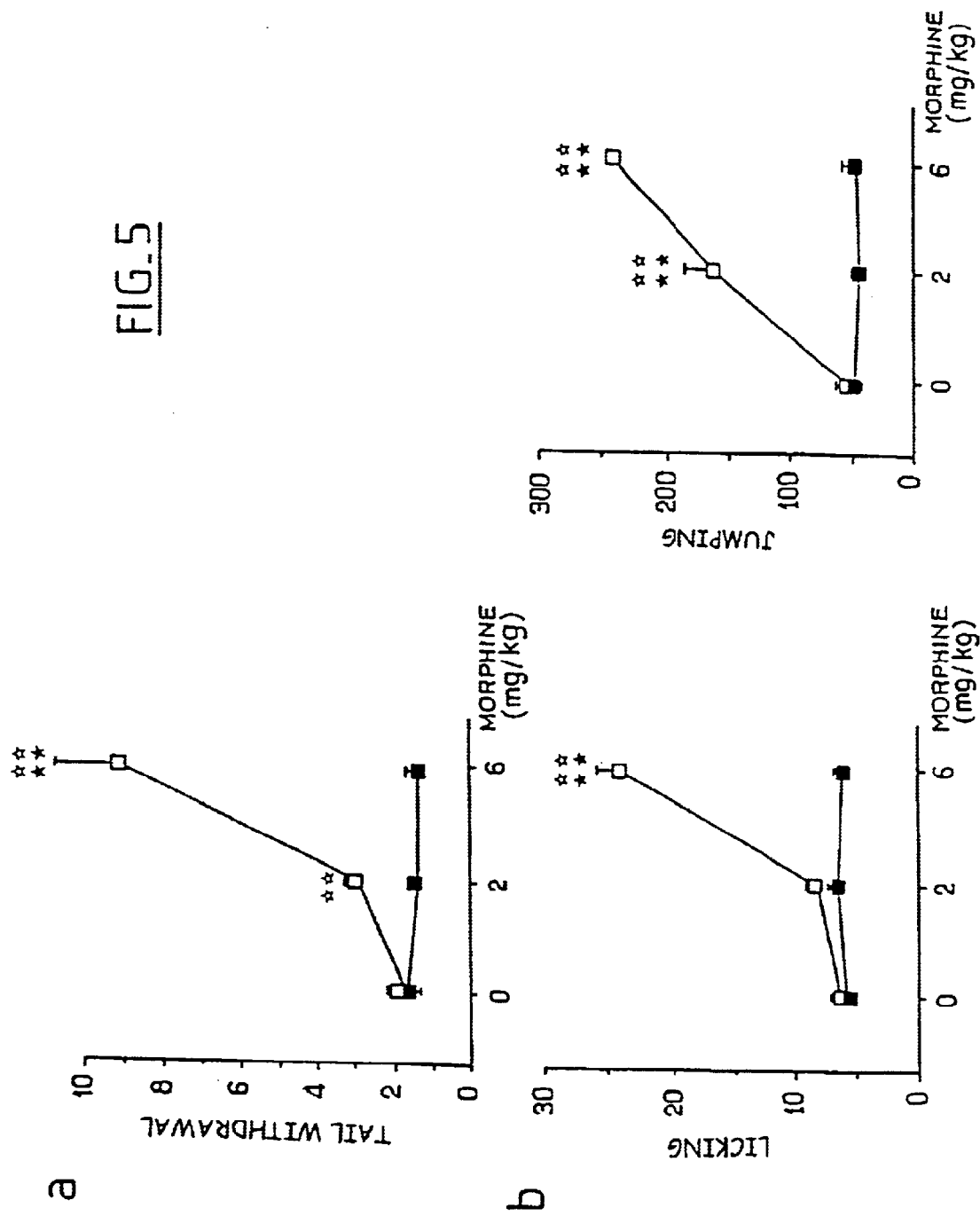

The pharmacological responses obtained after acute and chronic administration of morphine are studied in mice deficient in the $\mu$ opioid receptor. In a first experiment, the antinociceptive effects induced by an acute injection of morphine (2 and 6 mg/kg, subcutaneous) are evaluated in the tail immersion test (latency of withdrawal of the tail) and hot plate test (latency of licking and jumping). The nociceptive threshold of mutant and wild-type mice is the same in the various parameters evaluated in the two tests, suggesting the absence of involvement of the $\mu$ receptor in the basal nociceptive perception. In the wild-type mice, administration of morphine induces significant antinociceptive responses in the tail immersion test, and in the licking and jumping of the hot plate test. In the mutants, no antinociceptive response is induced by morphine in any of the nociceptive thresholds (FIG. 5).

In a second experiment, the reinforcing properties of morphine are investigated in the same group of animals using the paradigm of conditioning to the position (Valverde et al., (1996) Psychopharmacology 123:119–126). The administration of morphine induces a conditioned preference of position in wild-type mice, as shown by a significant increase in the time spent in the compartment associated with morphine during the test phase. This conditioned behaviour is not observed in mutant mice, which spend the same time in the compartment intended for morphine in the conditioning phases (FIG. 6). The response found in this test is probably due to a loss in the auto-recompense properties of morphine in mice deficient in the $\mu$ opioid receptor.

Figure 7A:
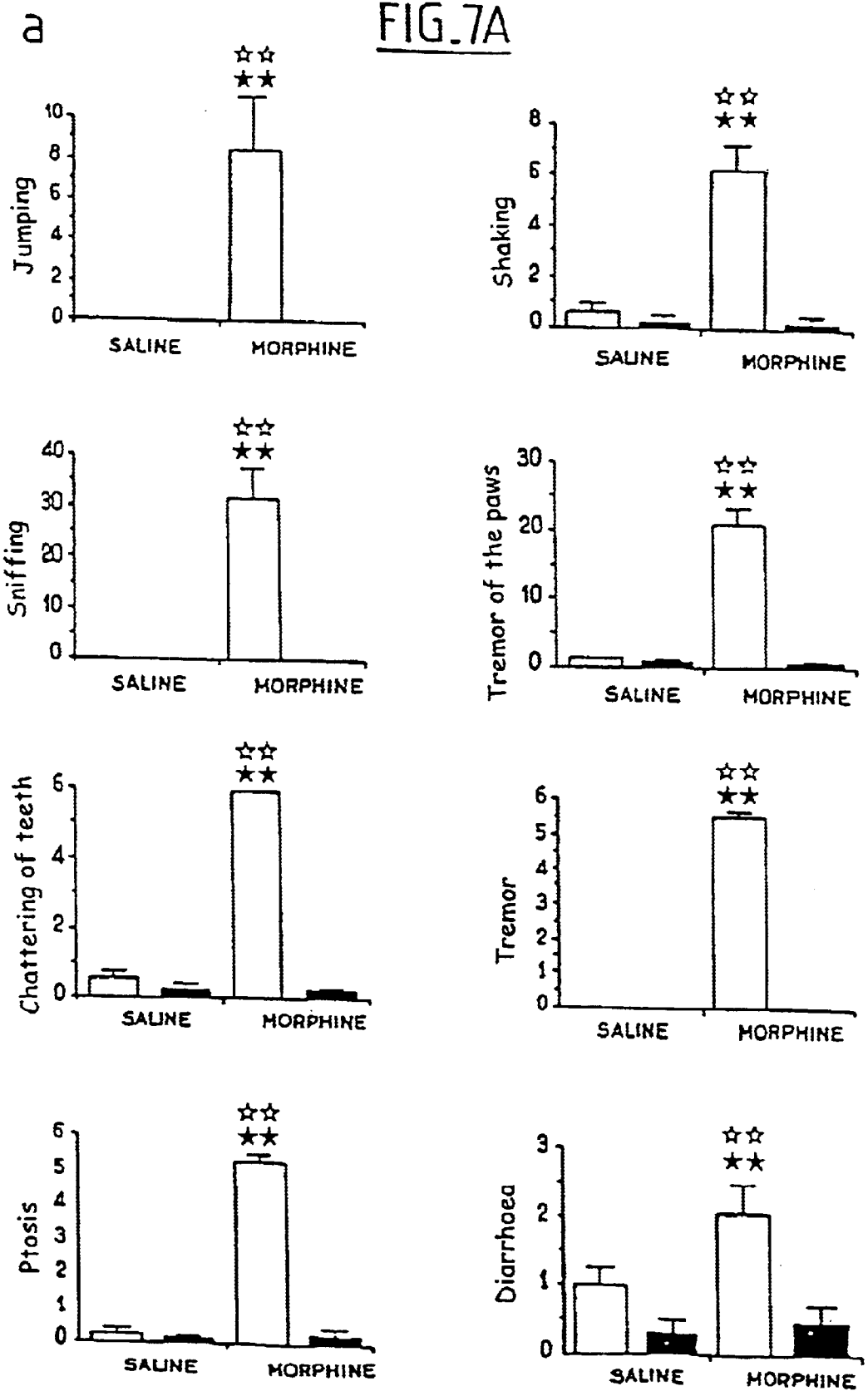

In a third experiment, a significant degree of dependence is induced by giving increased doses of morphine, and the manifestation of symptoms (somatic) of deficiency is evaluated after administration of naloxone. After chronic treatment with morphine, the wild-type mice but not the mutants show the classical symptoms of rodents treated with opiates, such as the Straub reflex and increased locomotor activity. The administration of naloxone does not change the behaviour in the controls to which a saline solution has been administered, and induces the various behavioural symptoms of deficiency in the wild animals treated with morphine (FIG. 7). In the mutant animals treated chronically with morphine, the injection of naloxone induces no modification in behaviour, showing the absence of the dependence on morphine in mice deficient in the μ opioid receptor.

Chronic treatment with opiates increases the response of the transmission route of the cyclic AMP signal specifically in the zones of the brain involved in tolerance to opiates and dependence (locus coeruleus, amygdales, striatum) (Terwilliger, R. Z., Beitner-Johnson, D., Severino. K. A., Crain. S. M. and Nestler, E. J. Brain Res., 548:100–110 (1991); Duman, R. S., Tallman, J. F. and Nestler, E. J. J. Pharmacol. Exp. Ther. 246:1033–1039 (1988), a phenomenon which is thought to be involved in the deficiency syndrome (Nestler, E. J., Hope. B. T. and Widnell, K. L. Neuron, 11:995–1006 (1993)). To provide a biochemical basis for the last observation in behaviour, the basal adenylate cyclase activity was quantified and stimulated by forskolin in the striatum of wild mice and deficient mice after morphine deficiency induced by naloxone. Statistical analysis shows a significant interaction (correlation) between the treatment with morphine and the +/+ genotype for both the basal adenylate cyclase activity ($F(1,12)=7.15$, $p=0.0203$) and that stimulated by forskolin ($F(1,12)=7.36$, $p=0.0189$). Administration of naloxone after chronic treatment with morphine thus results in an adenylate cyclase activity in the striatum which increased by 30% in wild mice, according to the previous observations (Terwilliger, R. Z., Beitner-Johnson, D., Severino. K. A., Crain. S. M. and Nestler, E. J. Brain Res., 548:100–110 (1991)). On the other hand, the increase in the cyclase activity is absent in the animals deficient in the μ receptor. The activity of adenylate cyclase in the cerebellum, a region naturally deficient in μ receptors, was used as a negative control, and no significant change between the various groups was found. This result suggests that the absence of the μ receptor in the homozygous mutant animals prevents development of the adenylate cyclase activity and supports the hypothesis according to which the increase in the cyclic AMP route is involved in abstinence from opiates.

TABLE 1

Adenylate cyclase activity, basal and stimulated by forskolin (FK, 100 mM) in homogenates of the striatum and cerebellum from wild mice (+/+) and homozygous deficient mice (−/−) after morphine deficiency induced by naloxone. The results are expressed in pmoles of cyclic AMP formed/minute/mg of protein and show the mean ± SD of four individual experiments carried out in triplicate. The star indicates $p < 0.05$, compared with the control (saline solution).

|  | μ +/+ | | μ −/− | |
| --- | --- | --- | --- | --- |
|  | Saline | Morphine | Saline | Morphine |
| STRIATUM | | | | |
| Basal | 278 ± 23 | 401 ± 22* | 304 ± 16 | 304 ± 28 |
| FK | 1130 ± 71 | 1473 ± 43* | 1196 ± 40 | 1158 ± 108 |
| CEREBELLUM | | | | |
| Basal | 235 ± 35 | 209 ± 30 | 236 ± 17 | 213 ± 42 |
| FK | 1075 ± 115 | 966 ± 55 | 1068 ± 56 | 979 ± 73 |

Methods

The mice treated in a chronic manner (see FIG. 7) either with the saline solution or with the morphine receive a single injection of naloxone and are sacrificed 1 h later. The tissues are homogenized in 10 volumes of an ice-cooled buffer containing: Tris-HCl 20 mM, pH 8.0, EDTA 1 mM, DTT (dithiothreitol) 0.5 mM, PMSF (phenylmethylsulphonyl fluoride) 0.5 mM. The homogenates (40–100 μg protein) are incubated at 37° C. for 10 minutes in 60 μl of a test medium of the following composition: Tris 50 mM, pH 7.6, $MgCl_2$ 5 mM, cAMP 1 mM, ATP 100 μM containing 106 cpm ($\alpha\text{-}^{32}P$)-ATP, with a regeneration system consisting of 5 mM creatine phosphate and 250 mg/ml creatine kinase. The amount of $\alpha\text{-}^{32}P$-cAMP formed is measured after separation of the cAMP from the ATP on aluminium columns as described previously (Hanoune. J., Stengel, D., Lacombe, M. L., Feldman, G. and Coudrier, E. (1977) J. Biol. Chem. 252:2039–2045). The protein is determined using the Bio-Rad test (Bio-Rad, FRG). The statistical analysis is carried out using the general system of the linear model of the SAS program (Cary, N. C. (1989) in SAS Institute Inc.: SAS/STAT User's Guide version 6 (SAS Institute Corporation), vol. 1).

Conclusions

No obvious morphological anomaly is detected in these mice, which grow and reproduce normally and have a preserved circadian activity.

The binding sites of the opioid receptors (μ, δ and κ) were studied by analysis by saturation and by autoradiography mapping on sections of the brain and the figures for expression of the genes of endogenous opioid peptides (proenkephalin, prodynorphin and proopiomelanocortin) were analysed by hybridization in situ. A total absence of binding sites of the μ opioid receptors is shown in −/− mice, without a marked change in the number of δ and κ sites in these animals. The distribution of the expression of opioid peptides was analysed and it was found that no distinction can be made between wild-type and mutant mice. These observations indicate that compensatory changes are involved in the endogenous opioid system in the absence of the μ receptor.

An animal model for studying analgesia induced by opiates, auto-recompense and physical dependence is thus available. Pharmacological experiments in vitro and in vivo carried out previously had shown that the three sub-types of opioid receptors were involved in regulation of the nociceptive stimulus. Furthermore, both the μ and δ receptors are involved in the auto-recompense properties of opiates and are candidates for participation in the expression of the physical dependence on opiates. The aim of the present study is therefore to determine the contribution of the μ receptors in the response to opiates in vivo and to measure the behavioural response of animals, and we used morphine as the prototype opiate medicament.

The analgesia induced by morphine was studied using the tail immersion and hot plate tests, where the nociceptive response predominantly involves spinal and supraspinal mechanisms respectively. In the absence of the medicament, the pain thresholds are identical between the +/+and −/− mice, suggesting that the μ opioid receptor is not involved in maintaining normal pain perception, or that its physiological role can be compensated by other different mechanisms of the endogenous opioid system. Morphine induces a dose-dependent analgesiain the wild-type animals, but morphine has no effect at all in the mice deficient in the μ receptor. The absence of the response to morphine in the tail immersion test is particularly interesting and leads to reconsideration of the role of the other opioid receptors in spinal analgesia.

The auto-recompense properties of morphine in the paradigm of preference of position are also studied. The phenotype of mutant mice is clear: no conditioned preference of position is observed in the mutant mice, while morphine induces marked reinforcing effects in the wild-type mice.

A strong physical dependence is also induced by injection of increasing doses of morphine (up to 100 mg/kg), and the deficiency syndrome induced by injecting the non-specific opioid antagonist naloxone. In the wild-type mice, naloxone causes the classical somatic symptoms of deficiency, as well as loss in weight and hypothermia. On the other hand, the homozygous mice deficient in the $\mu$ receptor show no behavioural or vegetative symptoms of abstinence observed in the wild-type animals. In order to give biochemical support to these lasts results, the adenylate cyclase activity in the striatum of abstinent mice was measured. An increase in 30% of the basal adenylate cyclase activity and of that induced by forskolin was found in the wild-type mice deficient in morphine, as described previously in the literature. On the other hand, no modification in the levels of formation of cyclic AMP is observed in the mutant mice.

This set of results is of prime interest for understanding the biological action of opiate medicaments. The identification of the molecular target of morphine is provided by the present invention. It is also demonstrated that the activity of the MOR gene is absolutely essential for the analgesia induced by morphine, the auto-recompense effects and physical dependence. Furthermore, the present invention also shows that the $\delta$ and $\kappa$ receptors are not involved in the biological actions of morphine—even partly—in the absence of the $\mu$ receptor, although these receptors are expressed and bind to opioid ligands in the mutant mice. Consequently, the product of the gene of the $\mu$ opioid receptor is not only the preferred target of morphine, as described, but also a necessary component for the action of opiates. The present genetic approach shows for the first time the essential role of the opioid receptor $\mu$ in the multiple actions of opiates.

EXAMPLE 2

Creation of a Line of Mutant mice for Which the Gene Which Codes for the Kappa Opioid Receptor has been Interrupted by Homologous Recombination The gene which codes for the kappa opioid receptor of mice was obtained by screening a genomic DNA bank of SVJ129 mice (marketed by Stratagene, USA) with the aid of a probe of 231 base pairs (bp) which codes for amino acids 6 to 82 of the kappa receptor. Eight positive clones were obtained and the position of the first coding exon was mapped using standard techniques. A BamHI restriction fragment of 6.8 kilo-base pairs (kb, see FIG. 10) containing the first coding exon was sub-cloned in the pBluescript vector (Stratagene) in which the SmaI site had been destroyed beforehand. Two SmaI sites were then created by directed mutagenesis, one on the site of initiation of the transduction (CC<u>ATG</u>G into CCCGGG), the other at the 5' end of exon 1. These two sites thus enabled the site of initiation of the transduction (ATG) to be destroyed and a fragment of 234 bp containing the majority of the coding sequence contained in exon 1 to be eliminated (see FIG. 10). This fragment was replaced by a neo cassette containing the gene of resistance to neomycin, flanked by a 5' promoter and a 3' polyadenylation signal originating from the PGK (phosphoglycerate kinase) gene. The final vector (see figure) contains 1.3 kb in 5' and 5.2 kb in 3' of sequences of the kappa gene. This construction was electroporated in embryonal strain (ES) cells originating from mice of the line SV129. The cells were then selected for G418 and the resistant clones were sub-cloned. The genomic DNA of these clones was isolated and analysed by DNA transfer (Southern) using external 5' and 3' probes (see figure). The cells of one of positive clones was injected into the blastocysts of mice of the line C57/BL6 and chimaeric mice were obtained. These chimaeras, by crossing with C57/BL6 mice, enabled heterozygous mice to be obtained for the mutation, and crossing of these mice with one another then enabled the homozygous animals to be obtained. The genotype of the heterozygous and homozygous mice was determined by genomic (Southern) DNA transfer using external 5' and 3' probes.

The technical details are as follows:

The external 3' probe: corresponds to a BamHI/SacI restriction fragment of about 700 bp situated at 5.2 kb in 3' of exon 1 (see FIG. 10).

The external 5' probe: corresponds to an SacI/BamHI restriction fragment of about 600 bp situated at 1.3 kb of exon 1. The BamHI site of this fragment is naturally present in the gene of the kappa receptor (see FIG. 10). The SacI site (not shown on the figure) corresponds to a cloning site present in the $\lambda$FixII phage which was used to construct the genomic DNA bank of mice.

The binding sites of the $\kappa$, $\mu$ and $\delta$ receptors in the brains of mice which were wild +/+, heterozygous +/− and homozygous −/− and deficient in the gene of the kappa receptor were then analysed (see table below). Analysis by saturation of the binding of (3H) CI977 (selective kappa ligand) on homogenates of whole brains indicates a reduction of 50% of the binding sites of the kappa receptor in the heterozygous animals and a total loss of binding of the kappa ligand in the homozygous mutants. Furthermore, no change in the binding of the mu ligand (3H)DAGO and delta (3H)NTI and (3H)deltorphin I ligands in mutant animals with respect to wild animals was found, which indicates the absence of compensatory phenomena in the mu and delta receptors.

|  | CI977 Kd (nM) | Bmax (pmole/mg proteins) | DAGO Kd | Bmax | Deltorphin I Kd | Bmax | NTI Kd | Bmax |
|---|---|---|---|---|---|---|---|---|
| +/+ | 0.137 (0.001) | 0.040 (0.002) | 1.26 (0.24) | 0.153 (0.024) | 0.42 (0.02) | 0.089 (0.001) | 0.108 (0.020) | 0.204 (0.023) |
| +/− | 0.173 (0.004) | 0.020 (0.002) | 1.36 (0.11) | 0.146 (0.003) | 0.380 (0.004) | 0.099 (0.01) | 0.109 (0.028) | 0.170 (0.03) |
| −/− | undetectable | undetectable | 1.39 (0.12) | 0.139 (0.014) | 0.319 (0.07) | 0.090 (0.008) | 0.114 (0.010) | 0.190 (0.013) |

Autoradiography mapping studies of the binding of (3H) CI977 carried out on sections of the brain confirmed the absence of binding sites of the kappa receptor through the entire brain in the homozygous mice and a reduction of 50% in the heterozygous mice. Furthermore, the autoradiography studies of the binding of (3H) deltorphin I and (3H) DAGO showed that the distribution of these sites was not altered, confirming the absence of compensatory phenomena at the level of the delta and mu receptors. To determine whether the absence of kappa receptors can alter the expression of genes which code for the opioid peptides (enkephalins, dynorphins and beta-endorphin), an analysis of the level of messengers which code for these peptides was carried out by hybridization in situ on the brain of +/+, +/− and −/− animals. No modification was found in any of the regions analysed. In addition, it was shown that the homozygous mice for the mutation no longer show analgesia following the subcutaneous injection of a selective kappa agonist (U50488-H, 6 and 20 mg/kg), neither during the tail withdrawal test nor during the hot plate test.

All these results show the complete inactivation of the gene which codes for the kappa receptor.

The technical details are the following:

The protocols used to carry out the binding experiments on homogenates of the brain, the autoradiography studies, the hybridizations in situ and the behavioural tests are identical to those used for analysis of the animals for which the gene which codes for the mu receptor was interrupted (see example 1).

EXAMPLE 3

Creation of a Line of Mutant mice for Which the Gene Which Codes for the Delta Opioid Receptor has been Interrupted by Homologous Recombination A genomic bank of mice (ES SV 129/D3 cells) cloned in the vector EMBL3 was screened with a cDNA probe of mice. Several clones were obtained. The clone of phage 17.2, which has a size of 14.5 kb and which contains the first exon of the gene which codes for the delta opioid receptor, was used for construction of the vector for the homologous recombination in embryonal mice cells. A restriction map was first obtained around the first exon. The construction of the vector was carried out in four stages: (1) An EcoRI/NotI fragment of 7.2 kb containing the first exon of the gene of the delta opioid receptor was cloned in the pBluescript vector. (2) The first exon was taken by cutting this plasmid with the enzyme SmaI. (3) A fragment of 1.9 kb of the vector pKJ-1 (Lufkin, T., Dierich, A., LeMeur, M., Mark, M. and Chambon, P. (1991) Cell, 66:1105) containing the gene of resistance to neomycin under control of the promoter PGK is inserted at this place. (4) A NotI-SacI fragment of 1.3 kb of the clone of phage 17.2 is added upstream of this construction. The final construction is shown in FIG. 9 and has been verified by sequencing.

As regards the 5' probe, this is shown by probe 1 on FIG. 9 and corresponds to the SacI—SacI fragment (shown by probe 1 on FIG. 9) indicated on the restriction map of the gene.

As regards the 3' probe, this is shown by the fragment obtained by PCR situated between the EcoRI sites (see FIG. 9, probe 2). The oligonucleotides which have enabled these to be obtained are, respectively:

sense oligonucleotide: 5' AGGAAGCCTGGGTCTC-CTTC3' antisense oligonucleotide: 5' GTGCACCATGGGTGTG-CAGC3'

About 800 neomycin-resistant ES lines were screened by Southern blot using the probes described. One line was found to be positive for the mutation (insertion of the Neo gene at a good locus). These cells were injected into 205 blastocysts of C57/Black6 mice and reimplanted into 15 pseudogestant females. Eight gestations were conducted to term and gave rise to 48 chimaeric mice, 12 of which were male. These are crossed with C57/Black6 females to obtain heterozygous mice for the mutation.

What is claimed is:

1. A transgenic mouse homozygous for a disruption in the gene encoding the mu type opiate receptor, wherein an exon of said mu type opiate receptor gene is replaced by all or part of a marker gene wherein said disruption in said mouse results in the lack of a functional mu type opiate receptor in said mouse, and said mouse demonstrates no anticociceptive response induced by morphine in any of the nociceptive thresholds, an absence of dependence on morphine after chronic treatment and do not exhibit symptoms of deficiency such as reduced Straub reflex and increased locomotor activity upon withdrawal of administration.

2. The transgenic mouse according to claim 1, wherein said marker gene is the gene of resistance to neomycin (neo), inserted between two contiguous nucleotides of exon 2 of said mu type opiate receptor gene.

3. The transgenic mouse according to claim 2, wherein said gene of resistance to neomycin (neo) is under the control of the promoter phosphoglycerate kinase-1 (PGK-1).

4. A process for screening medicaments which act on pathologies involving opiate receptors, comprising:
   administering drugs to be tested to a transgenic mouse according to claim 1, or cells therefrom containing said disruption;
   determination of the nociceptive thresholds by the tail immersion and hot plate test after injection of the drugs to be tested,
   determination of the response to drugs to be tested by animals in which has been produced chronic pain induced by injection of irritating products, carrageenan and Freund's adjuvant, and producing monoarthritis or polyarthritis, or the test of sciatic nerve section, or the test of sciatic nerve ligation in the case of neuropathic pain,
   or determination of the psychotropic properties of drugs to be tested by the test of preference of position or of auto-administration, or determination of the level of physical dependence by induction of severe dependence and provocation of withdrawal in the case of toxicomania,
   or determination of the mixed lymphocyte reaction and of the duration of sufferance in the case of prevention or treatment of transplant rejection.

5. A process for obtaining a transgenic mouse according to claim 1, comprising
   replacing the endogenous gene of the opiate receptor of the mu type, by a construction comprising the gene of the opiate receptor of the mu type in which,
   exon 2 of the gene of the opiate receptor of the mu type is interrupted between two contiguous nucleotides by a portion of a marker gene, and
   introducing said cells into blastocytes of mice,
   selection of male chimaeric mice according to a criterion corresponding to an ES line,
   crossing of the selected mice with C57BL/6 mice, to obtain mice which are heterozygous with respect to a construction of a transgenic mouse or cells therefrom containing the gene of the opiate receptor of the mu type in which a fragment of the gene of the receptor containing an exon that is
   either replaced by all or part of a marker gene,
   or interrupted by the insertion between two contiguous nucleotides of all or part of a marker gene, the expression of the gene of the mu type being disrupted relative to expression by a non-transgenic mouse; and
   crossing of two heterozygotes to obtain a mouse which is homozygous with respect to said construction.

6. A transgenic mouse homozygous for a disruption in the gene encoding the kappa type opiate receptor, wherein an exon of said kappa type opiate receptor gene is replaced by all or part of a marker gene wherein said disruption in said mouse results in the lack of a functional kappa type opiate receptor in said mouse, and said mouse demonstrates no binding of the kappa selective ligand (3H)CI977 and no analgesia following subcutaneous injection of the selective kappa agonist US0488-H.

7. The transgenic mouse according to claim 6, wherein said marker gene is the gene of resistance to neomycin (neo), inserted in exon 1 of said kappa type opiate receptor gene.

8. A process for screening medicaments which act on pathologies involving opiate receptors, comprising:
   administering drugs to be tested to a transgenic mouse according to claim 6, or cells therefrom containing said disruption;
   determination of the nociceptive thresholds by the tail immersion and hot plate test after injection of the drugs to be tested, determination of the response to drugs to be tested by animals in which has been produced chronic pain induced by injection of irritating products, carrageenan and Freund's adjuvant, and producing monoarthritis or polyarthritis, or the test of sciatic nerve section, or the test of sciatic nerve ligation in the case of neuropathic pain, or determination of the psychotropic properties of drugs to be tested by the test of preference of position or of auto-administration, or determination of the level of physical dependence by induction of severe dependence and provocation of withdrawal in the case of toxicomania, or determination of the mixed lymphocyte reaction and of the duration of sufferance in the case of prevention or treatment of transplant rejection.

9. A process for obtaining a transgenic mouse according to claim 6, comprising replacement of the endogenous gene of the opiate receptor of the kappa type in cells of mice, by a construction comprising the gene of the opiate receptor of the kappa type in which, a fragment containing exon 1 of the gene of the opiate receptor of the kappa type is replaced by a marker, and introduction of the said cells into blastocytes of mice, selection of male chimaeric mice according to a criterion corresponding to an ES line, crossing of the selected mice with C57BL/6 mice, to obtain mice which are heterozygous with respect to a construction of a transgenic mouse or cells therefrom containing the gene of the opiate receptor of the kappa type in which a fragment of the gene of the receptor containing an exon that is either replaced by all or part of a marker gene, or interrupted by the insertion between two contiguous nucleotides of all or part of a marker gene, the expression of the gene of the kappa type being disrupted relative to expression by a non-transgenic mouse; and crossing of two heterozygotes to obtain a mouse which is homozygous with respect to said construction.

10. A transgenic mouse homozygous for a disruption in the gene encoding the delta type opiate receptor, wherein an exon of said delta type opiate receptor gene is replaced by all or part of a marker gene wherein said disruption in said mouse results in the lack of a functional delta type opiate receptor in said mouse, and said mouse demonstrates no binding of the delta selective ligand naltrindole.

11. The transgenic mouse according to claim 10, wherein said marker gene is the gene of resistance to neomycin (neo), inserted in exon 1 of said delta type opiate receptor gene.

12. A process for screening medicaments which act on pathologies involving opiate receptors, comprising:

administering to a transgenic mouse according to claim 10, or cells therefrom containing said disruption;

determination of the nociceptive thresholds by the tail immersion and hot plate test after injection of the drugs to be tested, determination of the response to drugs to be tested by animals in which has been produced chronic pain induced by injection of irritating products, carrageenan and Freund's adjuvant, and producing monoarthritis or polyarthritis, or the test of sciatic nerve section, or the test of sciatic nerve ligation in the case of neuropathic pain, or determination of the psychotropic properties of drugs to be tested by the test of preference of position or of auto-administration, or determination of the level of physical dependence by induction of severe dependence and provocation of withdrawal in the case of toxicomania, or determination of the mixed lymphocyte reaction and of the duration of sufferance in the case of prevention or treatment of transplant rejection.

13. A process for obtaining a mouse according to claim 10, comprising replacement of the endogenous gene of the opiate receptor of the delta type in cells of mice, by a construction comprising the gene of the opiate receptor of the delta type in which, a fragment containing exon 1 of the gene of the opiate receptor of the delta type is replaced by a marker gene, and introduction of the said cells into blastocytes of mice, selection of male chimaeric mice according to a criterion corresponding to an ES line, crossing of the selected mice with C57BL/6 mice, to obtain mice which are heterozygous with respect to a construction of a transgenic mouse or cells therefrom containing the gene of the opiate receptor of the delta type in which a fragment of the gene of the receptor containing an exon that is either replaced by all or part of a marker gene, or interrupted by the insertion between two contiguous nucleotides of all or part of a marker gene, the expression of the gene of the delta type being disrupted relative to expression by a non-transgenic mouse; and crossing of two heterozygotes to obtain a mouse which is homozygous with respect to said construction.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 2229 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 256..1449

(xi) SEQUENCE DESCRIPTION: SEQ ID NO: 1:

```
CGGATCCTTA GCATCCCCAA AGCGCCTCCG TGTACTTCTA AGGTGGGAGG GGGATACAAG      60

CAGAGGAGAA TATCGGACGC TCAGACGTTC CATTCTGCCT GCCGCTCTTC TCTGGTTCCA     120

CTAGGGCTTG TCCTTGTAAG AAACTGACGG AGCCTAGGGC AGCTGTGAGA GGAAGAGGCT     180

GGGGCGCCTG GAACCCGAAC ACTCTTGAGT GCTCTCAGTT ACAGCCTACC GAGTCCGCAG     240
```

```
CAAGCATTCA GAACC ATG GAC AGC AGC GCC GGC CCA GGG AAC ATC AGC GAC       291
                 Met Asp Ser Ser Ala Gly Pro Gly Asn Ile Ser Asp
                  1               5                  10

TGC TCT GAC CCC TTA GCT CCT GCA AGT TGG TCC CCA GCA CCT GGC TCC        339
Cys Ser Asp Pro Leu Ala Pro Ala Ser Trp Ser Pro Ala Pro Gly Ser
            15                  20                  25

TGG CTC AAC TTG TCC CAC GTT GAT GGC AAC CAG TCC GAC CCA TGC GGT        387
Trp Leu Asn Leu Ser His Val Asp Gly Asn Gln Ser Asp Pro Cys Gly
        30                  35                  40

CCT AAC CGC ACG GGG CTT GGC GGG AGC CAC AGC CTG TGC CCT CAG ACC        435
Pro Asn Arg Thr Gly Leu Gly Gly Ser His Ser Leu Cys Pro Gln Thr
45                  50                  55                  60

GGC AGC CCT TCC ATG GTC ACA GCC ATC ACC ATC ATG GCC CTC TAT TCT        483
Gly Ser Pro Ser Met Val Thr Ala Ile Thr Ile Met Ala Leu Tyr Ser
                65                  70                  75

ATC GTG TGT GTA GTG GGC CTC TTT GGA AAC TTC CTG GTC ATG TAT GTG        531
Ile Val Cys Val Val Gly Leu Phe Gly Asn Phe Leu Val Met Tyr Val
            80                  85                  90

ATT GTA AGA TAT ACC AAA ATG AAG ACT GCC ACC AAC ATC TAC ATT TTC        579
Ile Val Arg Tyr Thr Lys Met Lys Thr Ala Thr Asn Ile Tyr Ile Phe
        95                  100                 105

AAC CTT GCT CTG GCA GAT GCC TTA GCC ACT AGC ACG CTG CCC TTT CAG        627
Asn Leu Ala Leu Ala Asp Ala Leu Ala Thr Ser Thr Leu Pro Phe Gln
110                 115                 120

AGT GTT AAC TAC CTG ATG GGA ACG TGG CCC TTT GGA AAC ATC CTC TGC        675
Ser Val Asn Tyr Leu Met Gly Thr Trp Pro Phe Gly Asn Ile Leu Cys
125                 130                 135                 140

AAG ATC GTG ATC TCA ATA GAC TAC TAC AAC ATG TTC ACC AGT ATC TTC        723
Lys Ile Val Ile Ser Ile Asp Tyr Tyr Asn Met Phe Thr Ser Ile Phe
                145                 150                 155

ACC CTC TGC ACC ATG AGT GTA GAC CGC TAC ATT GCC GTC TGC CAC CCG        771
Thr Leu Cys Thr Met Ser Val Asp Arg Tyr Ile Ala Val Cys His Pro
            160                 165                 170

GTC AAG GCC CTG GAT TTC CGT ACC CCC CGA AAT GCC AAA ATT GTC AAT        819
Val Lys Ala Leu Asp Phe Arg Thr Pro Arg Asn Ala Lys Ile Val Asn
        175                 180                 185

GTC TGC AAC TGG ATC CTC TCT TCT GCC ATT GGT CTG CCC GTA ATG TTC        867
Val Cys Asn Trp Ile Leu Ser Ser Ala Ile Gly Leu Pro Val Met Phe
    190                 195                 200

ATG GCA ACC ACA AAA TAC AGG CAG GGG TCC ATA GAT TGC ACC CTC ACT        915
Met Ala Thr Thr Lys Tyr Arg Gln Gly Ser Ile Asp Cys Thr Leu Thr
205                 210                 215                 220

TTC TCT CAT CCC ACA TGG TAC TGG GAG AAC CTG CTC AAA ATC TGT GTC        963
Phe Ser His Pro Thr Trp Tyr Trp Glu Asn Leu Leu Lys Ile Cys Val
                225                 230                 235

TTC ATC TTC GCC TTC ATC ATG CCG GTC CTC ATC ATC ACT GTG TGT TAT       1011
Phe Ile Phe Ala Phe Ile Met Pro Val Leu Ile Ile Thr Val Cys Tyr
            240                 245                 250

GGA CTG ATG ATC TTA CGA CTC AAG AGT GTC CGC ATG CTG TCG GGC TCC       1059
Gly Leu Met Ile Leu Arg Leu Lys Ser Val Arg Met Leu Ser Gly Ser
        255                 260                 265

AAA GAA AAG GAC AGG AAC CTG CGC AGG ATC ACC CGG ATG GTG CTG GTG       1107
Lys Glu Lys Asp Arg Asn Leu Arg Arg Ile Thr Arg Met Val Leu Val
270                 275                 280

GTC GTG GCT GTA TTT ATT GTC TGC TGG ACC CCC ATC CAC ATC TAT GTC       1155
Val Val Ala Val Phe Ile Val Cys Trp Thr Pro Ile His Ile Tyr Val
285                 290                 295                 300

ATC ATC AAA GCA CTG ATC ACG ATT CCA GAA ACC ACT TTC CAG ACT GTT       1203
Ile Ile Lys Ala Leu Ile Thr Ile Pro Glu Thr Thr Phe Gln Thr Val
            305                 310                 315
```

```
TCC TGG CAC TTC TGC ATT GCC TTG GGT TAC ACA AAC AGC TGC CTG AAC    1251
Ser Trp His Phe Cys Ile Ala Leu Gly Tyr Thr Asn Ser Cys Leu Asn
            320                 325                 330

CCA GTT CTT TAT GCG TTC CTG GAT GAA AAC TTC AAA CGA TGT TTT AGA    1299
Pro Val Leu Tyr Ala Phe Leu Asp Glu Asn Phe Lys Arg Cys Phe Arg
            335                 340                 345

GAG TTC TGC ATC CCA ACT TCC TCC ACA ATC GAA CAG CAA AAC TCT GCT    1347
Glu Phe Cys Ile Pro Thr Ser Ser Thr Ile Glu Gln Gln Asn Ser Ala
            350                 355                 360

CGA ATC CGT CAA AAC ACT AGG GAA CAC CCC TCC ACG GCT AAT ACA GTG    1395
Arg Ile Arg Gln Asn Thr Arg Glu His Pro Ser Thr Ala Asn Thr Val
365                 370                 375                 380

GAT CGA ACT AAC CAC CAG CTA GAA AAT CTG GAA GCA GAA ACT GCT CCA    1443
Asp Arg Thr Asn His Gln Leu Glu Asn Leu Glu Ala Glu Thr Ala Pro
                385                 390                 395

TTG CCC TAACTGGGTC CCACGCCATC CAGACCCTCG CTAAACTTAG AGGCTGCCAT     1499
Leu Pro

CTACTTGGAA TCAGGTTGCT GTCAGGGTTT GTGGGAGGCT CTGGTTTCCT GGAAAAGCAT  1559

CTGATCCTGC ATCATTCAAA GTCATTCCTC TCTGGCTATT CACGCTACAC GTCAGAGACA  1619

CTCAGACTGT GTCAAGCACT CAGAAGGAAG AGACTGCAGG CCACTACTGA ATCCAGCTCA  1679

TGTACAGAAA CATCCAATGG ACCACAATAC TCTGTGGTAT GTGATTTGTG ATCAACATAG  1739

AAGGTGACCC TTCCCTATGT GGAATTTTTA ATTTCAAGGA ATACTTATG ATCTCATCAA   1799

GGGAAAAATA GATGTCACTT GTTAAATTCA CTGTAGTGAT GCATAAAGGA AAAGCTACCT  1859

CTGACCTCTA GCCCAGTCAC CCTCTATGGA AGTTCCATA GGGAATATGT GAGGGAAAAT   1919

GTTGCTTCCA AATTAAATTT TCACCTTTAT GTTATAGTCT AGTTAAGACA TCAGGGGCAT  1979

CTCTGTTTCT TGGTTTTGTA TTGTTTGAAA GAAGACATCT TCCTCCCTAG CTGCGTGTTG  2039

AAAATGAAAG GGATTTAAAA CACAGTGTCA ACTGCAGAAT AGTTGATTCT CGCACTGAAG  2099

GGGGGGGGCT AATCTTCCCA ATTCTTTCCA TGTCCTCCAA GTGTTCACAA GGTCAAACTC  2159

AGAGTCACCC AGTAAGCTCA TCATGCCACC ATTCTGAGCA AAATCCTTGG ATTCCTGCTC  2219

AGAATGGTGG                                                         2229

(2) INFORMATION FOR SEQ ID NO: 2:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Ser Ser Ala Gly Pro Gly Asn Ile Ser Asp Cys Ser Asp Pro
1               5                   10                  15

Leu Ala Pro Ala Ser Trp Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
            85                  90                  95
```

```
Thr Lys Met Lys Thr Ala Thr Asn Ile Tyr Ile Phe Asn Leu Ala Leu
         100                 105                 110

Ala Asp Ala Leu Ala Thr Ser Thr Leu Pro Phe Gln Ser Val Asn Tyr
         115                 120                 125

Leu Met Gly Thr Trp Pro Phe Gly Asn Ile Leu Cys Lys Ile Val Ile
         130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                 165                 170                 175

Asp Phe Arg Thr Pro Arg Asn Ala Lys Ile Val Asn Val Cys Asn Trp
             180                 185                 190

Ile Leu Ser Ser Ala Ile Gly Leu Pro Val Met Phe Met Ala Thr Thr
             195                 200                 205

Lys Tyr Arg Gln Gly Ser Ile Asp Cys Thr Leu Thr Phe Ser His Pro
         210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                 245                 250                 255

Leu Arg Leu Lys Ser Val Arg Met Leu Ser Gly Ser Lys Glu Lys Asp
             260                 265                 270

Arg Asn Leu Arg Arg Ile Thr Arg Met Val Leu Val Val Val Ala Val
             275                 280                 285

Phe Ile Val Cys Trp Thr Pro Ile His Ile Tyr Val Ile Ile Lys Ala
         290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                 325                 330                 335

Ala Phe Leu Asp Glu Asn Phe Lys Arg Cys Phe Arg Glu Phe Cys Ile
             340                 345                 350

Pro Thr Ser Ser Thr Ile Glu Gln Gln Asn Ser Ala Arg Ile Arg Gln
         355                 360                 365

Asn Thr Arg Glu His Pro Ser Thr Ala Asn Thr Val Asp Arg Thr Asn
370                 375                 380

His Gln Leu Glu Asn Leu Glu Ala Glu Thr Ala Pro Leu Pro
385                 390                 395

(2) INFORMATION FOR SEQ ID NO: 3:

(i) SEQUENCE CHARACTERISTICS:
        (A) LENGTH: 2218 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 58..1173

(xi) SEQUENCE DESCRIPTION: SEQ ID NO: 3:

TCTAAAGGCT GGGTCCCTGC GCCCAGGGCG CACGGTGGAG ACGGACACGG CGGCGCC          57

ATG GAG CTG GTG CCC TCT GCC CGT GCG GAG CTG CAG TCC TCG CCC CTC        105
Met Glu Leu Val Pro Ser Ala Arg Ala Glu Leu Gln Ser Ser Pro Leu
```

```
                -continued 1                    5                    10                   15

GTC AAC CTC TCG GAC GCC TTT CCC AGC GCC TTC CCC AGC GCG GGC GCC       153
Val Asn Leu Ser Asp Ala Phe Pro Ser Ala Phe Pro Ser Ala Gly Ala
                    20                   25                   30

AAT GCG TCG GGG TCG CCG GGA GCC CGT AGT GCC TCG TCC CTC GCC CTA       201
Asn Ala Ser Gly Ser Pro Gly Ala Arg Ser Ala Ser Ser Leu Ala Leu
                35                   40                   45

GCC ATC GCC ATC ACC GCG CTC TAC TCG GCT GTG TGC GCA GTG GGG CTT       249
Ala Ile Ala Ile Thr Ala Leu Tyr Ser Ala Val Cys Ala Val Gly Leu
        50                   55                   60

CTG GGC AAC GTG CTC GTC ATG TTT GGC ATC GTC CGG TAC ACC AAA TTG       297
Leu Gly Asn Val Leu Val Met Phe Gly Ile Val Arg Tyr Thr Lys Leu
65                   70                   75                   80

AAG ACC GCC ACC AAC ATC TAC ATC TTC AAT CTG GCT TTG GCT GAT GCG       345
Lys Thr Ala Thr Asn Ile Tyr Ile Phe Asn Leu Ala Leu Ala Asp Ala
                    85                   90                   95

CTG GCC ACC AGC ACG CTG CCC TTC CAG AGC GCC AAG TAC TTG ATG GAA       393
Leu Ala Thr Ser Thr Leu Pro Phe Gln Ser Ala Lys Tyr Leu Met Glu
                100                  105                  110

ACG TGG CCG TTT GGC GAG CTG CTG TGC AAG GCT GTG CTC TCC ATT GAC       441
Thr Trp Pro Phe Gly Glu Leu Leu Cys Lys Ala Val Leu Ser Ile Asp
            115                  120                  125

TAC TAC AAC ATG TTC ACT AGC ATC TTC ACC CTC ACC ATG ATG AGC GTG       489
Tyr Tyr Asn Met Phe Thr Ser Ile Phe Thr Leu Thr Met Met Ser Val
        130                  135                  140

GAC CGC TAC ATT GCT GTC TGC CAT CCT GTC AAA GCC CTG GAC TTC CGG       537
Asp Arg Tyr Ile Ala Val Cys His Pro Val Lys Ala Leu Asp Phe Arg
145                  150                  155                  160

ACA CCA GCC AAG GCC AAG CTG ATC AAT ATA TGC ATC TGG GTC TTG GCT       585
Thr Pro Ala Lys Ala Lys Leu Ile Asn Ile Cys Ile Trp Val Leu Ala
                165                  170                  175

TCA GGT GTC GGG GTC CCC ATC ATG GTC ATG GCA GTG ACC CAA CCC CGG       633
Ser Gly Val Gly Val Pro Ile Met Val Met Ala Val Thr Gln Pro Arg
                180                  185                  190

GAT GGT GCA GTG GTA TGC ATG CTC CAG TTC CCC AGT CCC AGC TGG TAC       681
Asp Gly Ala Val Val Cys Met Leu Gln Phe Pro Ser Pro Ser Trp Tyr
            195                  200                  205

TGG GAC ACT GTG ACC AAG ATC TGC GTG TTC CTC TTT GCC TTC GTG GTG       729
Trp Asp Thr Val Thr Lys Ile Cys Val Phe Leu Phe Ala Phe Val Val
        210                  215                  220

CCG ATC CTC ATC ATC ACG GTG TGC TAT GGC CTC ATG CTA CTG CGC CTG       777
Pro Ile Leu Ile Ile Thr Val Cys Tyr Gly Leu Met Leu Leu Arg Leu
225                  230                  235                  240

CGC AGC GTG CGT CTG CTG TCC GGT TCC AAG GAG AAG GAC CGC AGC CTG       825
Arg Ser Val Arg Leu Leu Ser Gly Ser Lys Glu Lys Asp Arg Ser Leu
                245                  250                  255

CGG CGC ATC ACG CGC ATG GTG CTG GTG GTG GTG GGC GCC TTC GTG GTG       873
Arg Arg Ile Thr Arg Met Val Leu Val Val Val Gly Ala Phe Val Val
                260                  265                  270

TGC TGG GCG CCC ATC CAC ATC TTC GTC ATC GTC TGG ACG CTG GTG GAC       921
Cys Trp Ala Pro Ile His Ile Phe Val Ile Val Trp Thr Leu Val Asp
            275                  280                  285

ATC AAT CGG CGC GAC CCA CTT GTG GTG GCC GCA CTG CAC CTG TGC ATT       969
Ile Asn Arg Arg Asp Pro Leu Val Val Ala Ala Leu His Leu Cys Ile
        290                  295                  300

GCG CTG GGC TAC GCC AAC AGC AGC CTC AAC CCG GTT CTC TAC GCC TTC      1017
Ala Leu Gly Tyr Ala Asn Ser Ser Leu Asn Pro Val Leu Tyr Ala Phe
305                  310                  315                  320

CTG GAC GAG AAC TTC AAG CGC TGC TTC CGC CAG CTC TGT CGC ACG CCC      1065
```

```
Leu Asp Glu Asn Phe Lys Arg Cys Phe Arg Gln Leu Cys Arg Thr Pro
            325                 330                 335

TGC GGC CGC CAA GAA CCC GGC AGT CTC CGT CGT CCC CGC CAG GCC ACC    1113
Cys Gly Arg Gln Glu Pro Gly Ser Leu Arg Arg Pro Arg Gln Ala Thr
            340                 345                 350

ACG CGT GAG CGT GTC ACT GCC TGC ACC CCC TCC GAC GGC CCG GGC GGT    1161
Thr Arg Glu Arg Val Thr Ala Cys Thr Pro Ser Asp Gly Pro Gly Gly
            355                 360                 365

GGC GCT GCC GCC TGACCTACCC GACCTTCCCC TTAAACGCCC CTCCCAAGTG        1213
Gly Ala Ala Ala
        370

AAGTGATCCA GAGGCCACAC CGAGCTCCCT GGGAGGCTGT GGCCACCACC AGGACAGCTA  1273

GAATTGGGCC TGCACAGAGG GGAGGCCTCC TGTGGGACG GGGCCTGAGG GATCAAAGGC   1333

TCCAGGTTGG AACGGTGGGG GTGAGGAAGC AGAGCTGGTG ATTCCTAAAC TGTATCCATT  1393

AGTAAGGCCT CTCCAATGGG ACAGAGCCTC CGCCTTGAGA TAACATCGGG TTCTGGCCTT  1453

TTTGAACACC CAGCTCCAGT CCAAGACCCA AGGATTCCAG CTCCAGGAAC CAGGAGGGGC  1513

AGTGATGGGG TCGATGATTT GGTTTGGCTG AGAGTCCCAG CATTTGTGTT ATGGGGAGGA  1573

TCTCTCATCT TAGAGAAGAT AAGGGGACAG GGCATTCAGG CAAGGCAGCT TGGGGTTTGG  1633

TCAGGAGATA AGCGCCCCCT TCCCTTGGGG GGAGGATAAG TGGGGATGG TCAACGTTGG   1693

AGAAGAGTCA AAGTTCTCAC CACCTTTCTA ACTACTCAGC TAAACTCGTT GAGGCTAGGG  1753

CCAACGTGAC TTCTCTGTAG AGAGGATACA AGCCGGGCCT GATGGGGCAG GCCTGTGTAA  1813

TCCCAGTCAT AGTGGAGGCT GAGGCTGGAA AATTAAGGAC CAACAGCCTG GGCAATTTAG  1873

TGTCTCAAAA TAAAATGTAA AGAGGGCTGG GAATGTAGCT CAGTGGTAGG GTGTTTGTGT  1933

GAGGCTCTGG GATCAATAAG ACAAAACAAC CAACCAACCA AAAACCTTCC AAACAACAAA  1993

ACCAACCCTC AAACCAAAAA ACTATGTGGG TGTCTCTGAG TCTGGTTTGA AGAGAACCCG  2053

CAGCCCTGTA TCCCTGTGGG GCTGTGGACA GTGGGCAGAA GCAGAGGCTC CCTGGATCCT  2113

GAACAAGGGC CCCAAAAGCA AGTTCTAAAG GGACCCCTGA AACCGAGTAA GCCTTTGTGT  2173

CAAGAAGTGG GAGTACAACC AGAAAGGTGG CTGAGTGCTT TAGAG              2218

(2) INFORMATION FOR SEQ ID NO: 4:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO: 4:

Met Glu Leu Val Pro Ser Ala Arg Ala Glu Leu Gln Ser Ser Pro Leu
1               5                   10                  15

Val Asn Leu Ser Asp Ala Phe Pro Ser Ala Phe Pro Ser Ala Gly Ala
            20                  25                  30

Asn Ala Ser Gly Ser Pro Gly Ala Arg Ser Ala Ser Ser Leu Ala Leu
        35                  40                  45

Ala Ile Ala Ile Thr Ala Leu Tyr Ser Ala Val Cys Ala Val Gly Leu
    50                  55                  60

Leu Gly Asn Val Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
            85                  90                  95
```

```
Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
    210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Val Gly Ala Phe Val Val
            260                 265                 270

Cys Trp Ala Pro Ile His Ile Phe Val Ile Val Trp Thr Leu Val Asp
        275                 280                 285

Ile Asn Arg Arg Asp Pro Leu Val Val Ala Ala Leu His Leu Cys Ile
290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
            340                 345                 350

Thr Arg Glu Arg Val Thr Ala Cys Thr Pro Ser Asp Gly Pro Gly Gly
        355                 360                 365

Gly Ala Ala Ala
370

(2) INFORMATION FOR SEQ ID NO: 5:

(i) SEQUENCE CHARACTERISTICS:
        (A) LENGTH: 1408 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 184..1323

(xi) SEQUENCE DESCRIPTION: SEQ ID NO: 5:

GCACCTTGCT GATCCCAAAC AGGCAGAGCT TCTTCCAGTC TTGGAAGGCA CAAATTGAGC      60

ATCAGGAACG TGGACCCATC AGGGCTGAAC AGCTACTCAG GATCTAAAGT GGTGACTTGG     120

AAAGCTGACG TGACTTGGG AAGGGAGGTC GCCAATCAGC GATCTGGAGC TGCAGCGCTC     180

ACC ATG GAG TCC CCC ATT CAG ATC TTC CGA GGA GAT CCA GGC CCT ACC      228
    Met Glu Ser Pro Ile Gln Ile Phe Arg Gly Asp Pro Gly Pro Thr
```

```
                    1                    5                        10                       15
TGC TCT CCC AGT GCT TGC CTT CTC CCC AAC AGC AGC TCT TGG TTC CCC            276
Cys Ser Pro Ser Ala Cys Leu Leu Pro Asn Ser Ser Ser Trp Phe Pro
                    20                       25                   30

AAC TGG GCA GAA TCC GAC AGT AAT GGC AGT GTG GGC TCA GAG GAT CAG            324
Asn Trp Ala Glu Ser Asp Ser Asn Gly Ser Val Gly Ser Glu Asp Gln
                35                       40                       45

CAG CTG GAG TCC GCG CAC ATC TCT CCG GCC ATC CCT GTT ATC ATC ACC            372
Gln Leu Glu Ser Ala His Ile Ser Pro Ala Ile Pro Val Ile Ile Thr
            50                       55                       60

GCT GTC TAC TCT GTG GTA TTT GTG GTG GGC TTA GTG GGC AAT TCT CTG            420
Ala Val Tyr Ser Val Val Phe Val Val Gly Leu Val Gly Asn Ser Leu
        65                       70                       75

GTC ATG TTT GTC ATC ATC CGA TAC ACG AAG ATG AAG ACC GCA ACC AAC            468
Val Met Phe Val Ile Ile Arg Tyr Thr Lys Met Lys Thr Ala Thr Asn
80                       85                       90                   95

ATC TAC ATA TTT AAC CTG GCT TTG GCA GAT GCT TTG GTT ACT ACC ACT            516
Ile Tyr Ile Phe Asn Leu Ala Leu Ala Asp Ala Leu Val Thr Thr Thr
                    100                      105                     110

ATG CCC TTT CAG AGT GCT GTC TAC TTG ATG AAT TCT TGG CCT TTT GGA            564
Met Pro Phe Gln Ser Ala Val Tyr Leu Met Asn Ser Trp Pro Phe Gly
                115                      120                      125

GAT GTG CTA TGC AAG ATT GTC ATT TCC ATT GAC TAC TAC AAC ATG TTT            612
Asp Val Leu Cys Lys Ile Val Ile Ser Ile Asp Tyr Tyr Asn Met Phe
            130                      135                      140

ACC AGC ATA TTC ACC TTG ACC ATG ATG AGT GTG GAC CGC TAC ATT GCT            660
Thr Ser Ile Phe Thr Leu Thr Met Met Ser Val Asp Arg Tyr Ile Ala
        145                      150                      155

GTG TGC CAC CCT GTG AAA GCT TTG GAC TTC CGA ACA CCT TTG AAA GCA            708
Val Cys His Pro Val Lys Ala Leu Asp Phe Arg Thr Pro Leu Lys Ala
160                      165                      170                      175

AAG ATC ATC AAC ATC TGC ATT TGG CTC CTG GCA TCA TCT GTT GGT ATA            756
Lys Ile Ile Asn Ile Cys Ile Trp Leu Leu Ala Ser Ser Val Gly Ile
                    180                      185                      190

TCA GCG ATA GTC CTT GGA GGC ACC AAA GTC AGG GAA GAT GTG GAT GTC            804
Ser Ala Ile Val Leu Gly Gly Thr Lys Val Arg Glu Asp Val Asp Val
                195                      200                      205

ATT GAA TGC TCC TTG CAG TTT CCT GAT GAT GAA TAT TCC TGG TGG GAT            852
Ile Glu Cys Ser Leu Gln Phe Pro Asp Asp Glu Tyr Ser Trp Trp Asp
            210                      215                      220

CTC TTC ATG AAG ATC TGT GTC TTC GTC TTT GCC TTT GTG ATC CCA GTC            900
Leu Phe Met Lys Ile Cys Val Phe Val Phe Ala Phe Val Ile Pro Val
        225                      230                      235

CTC ATC ATC ATT GTC TGC TAC ACC CTG ATG ATC CTG CGC CTG AAG AGT            948
Leu Ile Ile Ile Val Cys Tyr Thr Leu Met Ile Leu Arg Leu Lys Ser
240                      245                      250                      255

GTC CGG CTC CTG TCT GGC TCC CGA GAG AAG GAC CGA AAT CTC CGC CGC            996
Val Arg Leu Leu Ser Gly Ser Arg Glu Lys Asp Arg Asn Leu Arg Arg
                    260                      265                      270

ATC ACC AAG CTG GTG CTG GTA GTA GTT GCA GTC TTC ATC ATC TGT TGG            1044
Ile Thr Lys Leu Val Leu Val Val Val Ala Val Phe Ile Ile Cys Trp
                275                      280                      285

ACC CCC ATT CAC ATC TTT ATC CTG GTG GAG GCT CTG GGA AGC ACC TCC            1092
Thr Pro Ile His Ile Phe Ile Leu Val Glu Ala Leu Gly Ser Thr Ser
            290                      295                      300

CAC AGC ACA GCT GCC CTC TCC AGC TAT TAT TTC TGT ATT GCC TTG GGT            1140
His Ser Thr Ala Ala Leu Ser Ser Tyr Tyr Phe Cys Ile Ala Leu Gly
        305                      310                      315

TAT ACC AAC AGC AGC CTG AAT CCT GTT CTC TAT GCC TTT CTG GAT GAA            1188
```

```
Tyr Thr Asn Ser Ser Leu Asn Pro Val Leu Tyr Ala Phe Leu Asp Glu
320                 325                 330                 335

AAC TTC AAG CGG TGT TTT AGG GAC TTC TGC TTC CCT ATT AAG ATG CGA      1236
Asn Phe Lys Arg Cys Phe Arg Asp Phe Cys Phe Pro Ile Lys Met Arg
                    340                 345                 350

ATG GAG CGC CAG AGC ACC AAT AGA GTT AGA AAC ACA GTT CAG GAT CCT      1284
Met Glu Arg Gln Ser Thr Asn Arg Val Arg Asn Thr Val Gln Asp Pro
                355                 360                 365

GCT TCC ATG AGA GAT GTG GGA GGG ATG AAT AAG CCA GTA TGACTAGTCG       1333
Ala Ser Met Arg Asp Val Gly Gly Met Asn Lys Pro Val
            370                 375                 380

TGGAAATGTC TTCTTATTGT TCTCCAGGTA GAGAAGAGTT CAATGATCTT GGTTTAACCC    1393

AGATTACAAC TGCAG                                                      1408

(2) INFORMATION FOR SEQ ID NO: 6:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 6:

Met Glu Ser Pro Ile Gln Ile Phe Arg Gly Asp Pro Gly Pro Thr Cys
1               5                   10                  15

Ser Pro Ser Ala Cys Leu Leu Pro Asn Ser Ser Trp Phe Pro Asn
            20                  25                  30

Trp Ala Glu Ser Asp Ser Asn Gly Ser Val Gly Ser Glu Asp Gln Gln
            35                  40                  45

Leu Glu Ser Ala His Ile Ser Pro Ala Ile Pro Val Ile Ile Thr Ala
        50                  55                  60

Val Tyr Ser Val Val Phe Val Val Gly Leu Val Gly Asn Ser Leu Val
65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Asp Val Ile
        195                 200                 205

Glu Cys Ser Leu Gln Phe Pro Asp Asp Glu Tyr Ser Trp Trp Asp Leu
210                 215                 220

Phe Met Lys Ile Cys Val Phe Val Phe Ala Phe Val Ile Pro Val Leu
225                 230                 235                 240

Ile Ile Ile Val Cys Tyr Thr Leu Met Ile Leu Arg Leu Lys Ser Val
                245                 250                 255
```

-continued

| | | | | | | | | | | | | |
|---|---|---|---|---|---|---|---|---|---|---|---|---|
|Arg|Leu|Leu|Ser 260|Gly|Ser|Arg|Glu|Lys 265|Asp|Arg|Asn|Leu|Arg 270|Arg|Ile|
|Thr|Lys|Leu 275|Val|Leu|Val|Val 280|Val|Ala|Val|Phe|Ile|Ile 285|Cys|Trp|Thr|
|Pro|Ile 290|His|Ile|Phe|Ile|Leu 295|Val|Glu|Ala|Leu|Gly 300|Ser|Thr|Ser|His|
|Ser 305|Thr|Ala|Ala|Leu|Ser 310|Ser|Tyr|Tyr|Phe|Cys 315|Ile|Ala|Leu|Gly|Tyr 320|
|Thr|Asn|Ser|Ser|Leu 325|Asn|Pro|Val|Leu|Tyr 330|Ala|Phe|Leu|Asp|Glu 335|Asn|
|Phe|Lys|Arg|Cys 340|Phe|Arg|Asp|Phe|Cys 345|Phe|Pro|Ile|Lys|Met 350|Arg|Met|
|Glu|Arg|Gln 355|Ser|Thr|Asn|Arg|Val 360|Arg|Asn|Thr|Val|Gln 365|Asp|Pro|Ala|
|Ser|Met|Arg 370|Asp|Val|Gly|Gly 375|Met|Asn|Lys|Pro|Val 380| | | | |